US005928879A

United States Patent [19]
Dumler et al.

[11] Patent Number: 5,928,879
[45] Date of Patent: *Jul. 27, 1999

[54] METHOD OF DIAGNOSING HUMAN GRANULOCYTIC EHRLICHIOSIS

[75] Inventors: J. Stephen Dumler, Ellicott City, Md.; Ulrike G. Munderloh, Falcon Heights, Minn.; John Madigan, Woodland, Calif.; Jesse Goodman, Minneapolis; Timothy J. Kurtti, Falcon Heights, both of Minn.

[73] Assignees: The Regents of the University of Minnesota, Minneapolis, Minn.; The Regents of the University of California, Oakland, Calif.; University of Maryland at Baltimore, Baltimore, Md.

[ * ] Notice: This patent issued on a continued prosecution application filed under 37 CFR 1.53(d), and is subject to the twenty year patent term provisions of 35 U.S.C. 154(a)(2).

[21] Appl. No.: 08/519,283

[22] Filed: Aug. 25, 1995

[51] Int. Cl.$^6$ .................................................. G01N 33/567
[52] U.S. Cl. .................. 435/7.21; 424/234.1; 424/265.1; 435/7.95; 435/40.52; 435/243; 435/366; 435/367; 435/372.1
[58] Field of Search .............................. 424/234.1, 265.1; 435/7.95, 366, 367, 372.1, 70.52, 7.21, 243

[56] References Cited

U.S. PATENT DOCUMENTS 5,192,679  3/1993  Dawson et al. .......................... 435/243

OTHER PUBLICATIONS

Collins et al. Nature. 1977. 270:347–349.
Ristic et al, Tribe II: Ehrlichieae Philip 1957, 948$^{AL}$, *Bergey's Manual of Systematic Bateriology*, 1:704–711, Eds Noel R. Kreig and John G. Holt, Williams and Wilkens Balto. (1984).
Rikihisa, "The Tribe *Ehrlichieae* and Ehrlichial Diseases", *Clin. Microbiol. Rev.*, 4:286–308 (1991).
Brodie et al, "Some Aspects of Tick–Borne Diseases of British Sheep", *The Veterinary Record*, 118:415–418 (1986).
Rodgers et al, "A Serological Survey of *Ehrlichia canis, Ehrlichia equi, Rickettsia rickettsii*, and *Borrelia burgdorferi* in Dogs in Oklahoma", *J. Vet. Diagn. Invest.*, 1:154–159 (1986).

"Human Granulocytic Ehrlichiosis", *Morsidity and Mortality Weekly Report*, 44(32):593–595 (1995).
Macleod et al, "Studies in Tick–Borne Fever of Sheep", *Parasitology*, 25:273–283 (1933).
Bakken et al, "Human Granulocytic Ehrlichiosis in the Upper Midwest United States", *JAMA*, 272(3):212–218 (1994).
Winjum et al, "In Vitro Proliferation of a Canine Granulocytic *Ehrlichia*", *Vet. Microbiology*, 34:355–362 (1993).
Munderloh et al, "Formulation of Medium for Tick Cell Culture", *Experimental and Applied Acarology*, 7:219–229 (1989).
Sells et al, "Ultrastructural Observations on *Ehrlichia equi* Organisms in Equine Granulocytes", *Infection and Immunity*, 13(1):273–280 (1976).
Chen et al, "Identification of a Granulocytotropic *Ehrlichia* Species as the Etiologic Agent of Human Disease", *J. of Clin. Microbiology*, 32(3):589–595 (1994).
Dumler et al, "Serologic Cross–Reactions Among *Ehrlichia equi, Ehrlichia phagocytophila*, and Human Granulocytic Ehrlichia", *J. of Clin. Microbiology*, 33(5):1098–1103 (1995).
Wysoki et al, "Spermatogenesis, Chromosomes and Sex Determination of Four Rhipicephalus Species (Acari: Ixodidae) from East Africa", *Genetica*, 48(3):233–238 (1978).
Sitbon et al, "Hemolytic Anemia and Erythroleukemia, Two Distinct Pathogenic Effects of Friend MuLV: Mapping of the Effects of Different Regions of the Viral Genome", *Cell*, 47:851–859 (1986).
Oliver et al, "Conspecificity of the Ticks *Ixodes scapularis* and *I. dammini* (Acari: Ixodidae)", *J. Med.Entomol.*, 30(1):54–63 (1993).
Madigan et al, "Seroepidemiologic Survey of Antibodies to *Ehrlichia equi* in horses of Northern California", *Javma*, 196(12):1962–1964 (1990).
Kurtti et al, "The Effects of 20–Hydroxyecdysone and Juvenile Hormone III on Tick Cells", *J. Parasitol.*, 69(6):1072–1078 (1983).

*Primary Examiner*—James C. Housel
*Assistant Examiner*—Jennifer Shaver
*Attorney, Agent, or Firm*—Sughrue, Mion, Zinn, Macpeak & Seas, PLLC

[57] ABSTRACT

Methods for the in vitro cultivation, propagation, and production of antigens of *Ehrlichia phagocytophila* genogroup granulocytic Ehrlichiae, including *Ehrlichia equi*, in *Ixodes scapularis* tick cell culture and in human HL60 promyelocytic leukemia cell culture.

5 Claims, 12 Drawing Sheets

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: synthetic (iii) HYPOTHETICAL: NO (xi) SEQUENCE DESCRIPTION: SEQ ID NO:1:

AACGGATTAT TCTTTATAGC TTGCT    25

(2) INFORMATION FOR SEQ ID NO:2:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: synthetic (iii) HYPOTHETICAL: NO (xi) SEQUENCE DESCRIPTION: SEQ ID NO:2:

GGAGATTAGA TCCTTCTTAA CGGAA    25

(2) INFORMATION FOR SEQ ID NO:3:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: synthetic (iii) HYPOTHETICAL: NO (xi) SEQUENCE DESCRIPTION: SEQ ID NO:3:

```
GTCGAACGGA TTATTCTTTA TAGCTTGC                                              28

(2) INFORMATION FOR SEQ ID NO:4:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: synthetic (iii) HYPOTHETICAL: NO (xi) SEQUENCE DESCRIPTION: SEQ ID NO:4:

CCCTTCCGTT AAGAAGGATC TAATCTCC                                              28

(2) INFORMATION FOR SEQ ID NO:5:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: synthetic (iii) HYPOTHETICAL: NO (xi) SEQUENCE DESCRIPTION: SEQ ID NO:5:

TAGATCCTTC TTAACGGAAG GGCG                                                  24

(2) INFORMATION FOR SEQ ID NO:6:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: synthetic (iii) HYPOTHETICAL: NO (xi) SEQUENCE DESCRIPTION: SEQ ID NO:6:

AAGTGCCCGG CTTAACCCGC TGGC                                                  24

(2) INFORMATION FOR SEQ ID NO:7:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: synthetic (iii) HYPOTHETICAL: NO (xi) SEQUENCE DESCRIPTION: SEQ ID NO:7:

TTTATCGCTA TTAGATGAGC CTATG                                                 25

(2) INFORMATION FOR SEQ ID NO:8:

(i) SEQUENCE CHARACTERISTICS:
         (A) LENGTH: 23 base pairs
         (B) TYPE: nucleic acid
         (C) STRANDEDNESS: single
         (D) TOPOLOGY: linear
```

```
    (ii) MOLECULE TYPE: synthetic (iii) HYPOTHETICAL: NO (xi) SEQUENCE DESCRIPTION: SEQ ID NO:8:

CTCTACACTA GGAATTCCGC TAT                                              23
```

METHOD OF DIAGNOSING HUMAN GRANULOCYTIC EHRLICHIOSIS

The work described herein was supported in part with funds from the Minnesota Agricultural Experiment Station (Project 377-3457), a Special Research Initiative Support Award from the University of Maryland School of Medicine, National Institutes of Health Grant No. AR 37909, and Equine Research Laboratory Grant No. 95-01 from the University of California, Davis.

FIELD OF THE INVENTION

The present invention relates to methods for the in vitro cultivation of granulocytic Ehrlichiae of the *Ehrlichia phagocytophila* genogroup in *Ixodes scapularis* tick cell culture and in human HL60 promyelocytic leukemia cell culture.

BACKGROUND OF THE INVENTION

Ehrlichiae are obligate intracellular bacteria that predominantly infect bone marrow-derived cells in their mammalian hosts. Those species, for which a biological vector is known, are transmitted by ticks. Typically, Ehrlichiae are contained within a membrane-lined vacuole of their host cell.

Ehrlichiae species were initially characterized on the basis of host cell type, host species, and serologic cross-reactivity. Ehrlichiae may be divided into three phylogenetically distinct groups on the basis of nucleotide sequences of the 16S ribosomal RNA genes in each species and strong serologic cross-reactions. Each group is denoted by the historical precedent for the genetic group.

The *Ehrlichia canis* group includes 3 species known to infect predominantly monocytes and macrophages, and a single species known to infect canine granulocytes. *Ehrlichia canis*, the type species, *E. chaffeensis*, and *E. muris* infect mononuclear phagocytes of dogs, humans, and mice, respectively, while *E. ewingii* infects canine granulocytes (Ristic et al, In: Bergey's manual of Systematic Bacteriology, 1(9):1957 (1984)).

The second genetic group, the *E. sennetsu* group, includes *E. sennetsu* and *E. risticii*. They are monocytic Ehrlichiae that are agents of human Sennetsu fever of Japan and Potomac horse fever (equine monocytic ehrlichiosis) of horses worldwide.

The third group, the *E. phagocytophila* (Ep) genogroup, includes the granulocytic Ehrlichiae, *E. equi*, the agent of equine granulocytic ehrlichiosis (EGE) of horses, and an agent of canine granulocytic ehrlichiosis in the US, South America, and Europe; *E. phagocytophila*, the agent of tick-borne fever of ruminants in Europe; an as yet unnamed Ehrlichiae that is the causative agent of human granulocytic ehrlichiosis (HGE) in the United States and Europe; and more distantly, *E. platys*, a thrombocytic Ehrlichiae that causes mild cyclical thrombocytopenia in dogs.

Emerging genetic and antigenic data indicates that the members of the *E. phagocytophila* genogroup are very closely related or identical species (Chen et al, *J. Clin. Microbiol.*, 32:589 (1994)). In humans, HGE was first recognized in 1990 (Chen et al, supra), and is considered an emerging disease of increasing clinical significance.

None of the granulocytic Ehrlichiae have been continuously propagated in vitro. This has continuously hampered the development of diagnostic tools for these infections, and investigation of the diseases and causative agents.

The clinical presentation of granulocytic ehrlichioses in man and animals are nonspecific and include fever, headache, rigors and malaise in humans, and fever, depression, and sometimes lameness in animals (Rikihisa, *Clin. Microbiol. Rev.*, 4:286 (1991)). Ehrlichiae infections have dramatic effects on the hematologic and hepatic systems, and most infected humans and animal species develop leukopenia, thrombocytopenia, anemia, and evidence of mild hepatic injury. The appearance of membrane-bound vacuoles containing the pathogens within circulating leukocytes is suggestive of the diagnosis. However, human patients and some animals infrequently present with infected leukocytes in the peripheral blood.

Tetracycline antibiotics are the drug of choice for treatment of all ehrlichioses, and most human patients respond with a dramatic defervescence after therapy (Dumler et al, *Clin. Infect. Dis.*, 20:1102 (1995)). In most cases, prevention of ehrlichioses focuses on vector control and prophylaxis using tetracyclines. The only agent for which a vaccine exists is *E. risticii*, which is cultivatable in vitro (Rikihisa, supra).

The exact economic toll extracted by the Ep group of Ehrlichiae is not known. In Great Britain, it is estimated that 2% of the entire goat population dies each year from secondary infections that occur only after *E. phagocytophila* infections (Brodie et al, *Vet. Rec.*, 118:415 (1986)). In the United States, equine and canine infections with *E. equi* have been infrequently documented because of the lack of suitable diagnostic tools and nonspecific presentation of the illness. However, with the recent recognition that the agent of HGE is nearly identical genetically (Chen et al, supra), and antigenically (Dumler, *J. Clin. Microbiol.*, 33:1098 (1995)), biologically with *E. equi*, and is capable of causing severe and fatal human infection, there has been an increased awareness of the prevalence of equine and canine infections. Serologic evidence of *E. equi* infection in some regions of California has been identified in up to 50% of the horses residing in those regions (Madigan et al, *J. Am. Vet. Med. Assoc.*, 196:1962 (1990)). Similarly, nearly 20% of animals tested in a serosurvey of ill dogs in Oklahoma had evidence of *E. equi* infection (Rodgers et al, *J. Vet. Diagn. Invest.*, 1:154 (1989)). Since the first identified case of HGE in 1990, there has been a logarithmic increase in the number of diagnoses of that human infection, especially since modern diagnostic methods have become available through specialized academic research facilities and some commercial laboratories. To date, approximately 115 cases of HGE have been recognized in the United States (Wormser et al, *MMWR*, 44:593 (1995)). Initial studies suggest that approximately 10% of human patients with Lyme disease may have been infected with the agent of HGE. Given the nearly 10,000 cases of Lyme disease reported annually in the United States, one would speculate that perhaps 1,000 of these patients may have also acquired undiagnosed HGE, in addition to those patients with HGE not accompanied by Lyme disease.

*Ehrlichia phagocytophila* and *E. equi* are transmissible through the bite of *Ixodes ricinus* (MacLeod et al, *Parasitology*, 25:273 (1933)) and *I. pacificus* ticks, respectively. Mounting evidence has implicated *Ixodes scapularis* (*dammini*) ticks as the vector responsible for transmitting the agent of HGE in the United States (Bakken et al, *JAMA*, 272:212 (1994)). It is assumed that larval ticks acquire the pathogen from a reservoir host, probably wild rodents, and that subsequent developmental stages, i.e., the nymphs and adults, transmit the Ehrlichiae during their blood meal.

Specific diagnosis of HGE, EGE, and tick-borne fever is accomplished by serology (Bakken et al, supra; Dumler, supra; and Madigan, supra), utilizing antigen prepared from infected animals. Diagnosis in animals is often suspected when typical intracytoplasmic inclusions are present in the peripheral blood leukocytes of febrile animals. In contrast, Ehrlichiae inclusions are variably present in the peripheral blood of humans who nevertheless may be very ill. As for other rickettsiae infections, the single most important determinant of clinical outcome is early diagnosis and early therapy with specific antimicrobial agents. If these patients are not treated promptly, the disease may quickly proceed to severe disease or a fatal outcome. Fatalities appear to be related to the development of secondary opportunistic infections that occur after the Ehrlichiae infection. Treatment with tetracycline antibiotics leads to a rapid therapeutic response (Bakken, supra).

Attempts to propagate *E. equi* and *E. phagocytophila* in vitro in primary neutrophils harvested from the peripheral blood of infected animals have yielded short term (48 to 72 hr) increases in the percentage of infected cells (Winjum et al, *Vet. Microbiol.*, 34:355 (1993)). However, supplementation of the cultures with additional primary, uninfected neutrophils is unable to provide a continuous propagation system. This finding implies that mature neutrophils are probably not competent to become infected, but that new cells become infected as immature cells, probably in the bone marrow. A search for a susceptible mammalian cell line has been fruitless so far, and other cell lines known to support the growth of other Ehrlichiae species, such as DH-82, P388$D_1$, U937, HEL, and Vero cells, do not support the growth of *E. equi* when co-cultivated with primary clinical samples.

Even more enigmatic is the biology of granulocytic Ehrlichiae in their tick vector. There is evidence, based on indirect immunofluorescent assays, that the organisms invade hemocytes of the tick, but other target tissues, if any, are unknown. By analogy with *Anaplasma marginale*, a related pathogen of cattle, it is expected that in the vector tick, a number of tissue types are invaded by *E. equi* and its relatives. Particularly, one can expect that the salivary glands of ticks should be invaded, as they would provide the rickettsiae with an obvious route of transmission to the mammal or to man. It is believed that culture systems for the production of the Ep group Ehrlichiae stages found in the mammal and in the vector would be valuable tools to elucidate the biology of these granulocytic Ehrlichiae in mammals, as well as in ticks, and would facilitate the development of appropriate diagnostic tools for HGE, and potentially an effective vaccine.

Because of the increasing prevalence and incidence of HGE and granulocytic ehrlichioses of horses and dogs, there is a need to develop reliable diagnostic tools that utilize antigen produced in vitro instead of in animals, such as horses. This capability will provide a more consistent, reproducible antigen for diagnosis, and will offer the ability for large scale production of both the mammalian stages and the vector stages in vitro.

SUMMARY OF THE INVENTION

This invention is directed to methods of growing or culturing Ep group granulocytic Ehrlichiae, such as *Ehrlichia equi*, in *Ixodes scapularis* cell culture and in human HL60 promyelocytic leukemia cell culture. The invention also includes Ehrlichiae products of growing Ehrlichiae in tick cell culture.

A method of the invention includes culturing Ep genogroup Ehrlichiae with an *Ixodes scapularis* cell line in a culture medium under conditions of reduced oxygen and increased $CO_2$ at a sufficient temperature until growth of the Ehrlichiae is detected. The culture medium comprises a medium suitable for the growth of invertebrate cells supplemented with an organic buffer, and a source of $HCO_3$ . Preferably, the cultures are incubated at a $CO_2$ level of about 3% to 5%, at a temperature of about 31° C. to 35° C. The organic buffer is preferably present at a concentration of about 10 to 15 mM. Concentrations of organic buffer of 25 mM or more are toxic to the invertebrate cells. The preferred cells are *Ixodes scapularis* cell line IDE8.

The tick cell cultures are incubated until growth of Ep group Ehrlichiae is detected. Ep group Ehrlichiae-infected tick cell cultures can be used as diagnostic tools for serodiagnosis. Ep group Ehrlichiae antigens can also be prepared from Ep group Ehrlichiae-infected tick cell culture. The antigen preparations are essentially free of horse antigens and pathogens.

A method of the invention also provides for growth of Ep group Ehrlichiae, such as *E. equi* in human myelocytic cell lines. *Ehrlichia equi*-infected cells, such as *E. equi*-infected IDE8 tick cells, are incubated with human HL60 promyelocyte leukemia cell line. Preferably, the cultures are incubated in medium with enhanced $CO_2$ of about 5% at a temperature of 37° C. The method is useful for preparation of Ep group Ehrlichiae antigens, such as *E. equi* antigens, that react with antibodies made by mammals and humans after infection by Ep group Ehrlichiae. Thus, the method is useful to prepare antigens for serodiagnostic applications.

BRIEF DESCRIPTION OF THE DRAWINGS

FIG. 1 represents an electron micrograph of *Ixodes scapularis* tick cell line IDE8 at passage 17.

FIG. 2 represents karyotypes of *Ixodes scapularis* tick cell lines IDE8, IDE12, ISE5 and ISE18 compared with the karyotype of a *Rhipicephalus appendiculatus* tick cell line, RAE25. Cultures were treated with colcemid over night, and chromosome spreads stained with Giemsa stain. Chromosomes of 100 metaphase sets were counted.

FIGS. 3A–3B show the banding patterns of the isoenzymes lactate dehydrogenase (LDH) (FIG. 3A); and malate dehydrogenase (MDH) (FIG. 3B), separated by isoelectric focussing. Tissue extracts from female ticks were compared with extracts from cell lines isolated from *I. scapularis* and *R. appendiculatus* (RAE25). The major band with a pI value of 8.1 is present in extracts from *I. scapularis* ticks and *I. scapularis* cell lines. The pI values of standard enzymes are indicated between the panels. Plus (+) denotes the position of the anode, and minus (–) the position of the cathode.

FIG. 4 shows the isoelectric focussing patterns of malic enzyme (ME) in tissue extracts from *I. scapularis* female ticks and cell lines IDE1, IDE2, IDE8 and IDE12; and ISE5 and ISE18 from *I. scapularis*; and RAE25 from *R. appendiculatus*. The major bands with pI values of 6.0, 6.3 and 6.5 are present in extracts from *I. scapularis* ticks and *I. scapularis* cell lines. The pI values of standard enzymes are indicated at the right margin. Plus (+) denotes the position of the anode, and minus (–), the position of the cathode.

FIG. 5 shows an ethidium bromide-stained gel of an *E. equi* DNA fragment amplified with primers that are specific for *E. equi, E. phagocytophila*, and the agent of HGE. Lane A, IDE8 tick cell culture infected with *E. equi*; lane B, uninfected IDE8 tick cell culture; lane C, plasmid pEe16SWG, a plasmid containing the entire 16S ribosomal RNA gene of *E. equi*; and lane D, no DNA template (water only); the far right lane represents the molecular size marker, and the molecular size of the amplified DNA is indicated on the left in base pairs.

FIGS. 6A–6B show the appearance of *Ehrlichia equi* in tick cells, line IDE8, cultured in vitro. FIG. 6A shows Giemsa-stained smear of IDE8 cells infected with *E. equi* passaged three times in vitro. FIG. 6B shows an electron micrograph of *E. equi* in tick cell line IDE8 passaged two times in vitro. "N" signifies the nucleus. Infected IDE8 cells were centrifuged for 10 min at 150×g, and the pellet fixed twice in a fixative as described by Sitbon et al, *Cell*, 47:851–859 (1986).

FIGS. 7A–7F show immuncytologic staining of *E. equi*-infected IDE8 tick cells before first passage in vitro. Infected tick cells were harvested and fixed on glass slide before reaction with human anti-HGE agent (FIG. 7A) and equine anti-*E. equi* (FIG. 7B) sera. Non-immune human serum (FIG. 7C) and non-immune equine serum (FIG. 7D) were used as controls. Anti-HGE agent (FIG. 7E) and anti-*E. equi* (FIG. 7F) antibodies and were also reacted with uninfected IDE8 tick cells as controls. All stains were performed by the immunoalkaline phosphatase method using naphthol phosphate and fast red as substrate with hematoxylin counterstain; magnification of each panel is X1200.

FIGS. 8A–8B show the appearance of *E. equi* in human HL60 cells cultured in vitro, and then stained with Giemsa stain. The intracytoplasmic aggregates of small, pleomorphic bacteria seemingly sequestered within a vacuole that together comprise the "morula".

FIGS. 9A and 9B show Ab immunofluorescent staining of *E. equi*-infected human HL60 cells propagated in vitro. An indirect fluorescent antibody stain was applied using serum from a patient convalescent from HGE. FIG. 9A shows cells with multiple and single morulae. FIG. 9B includes cells whose cytoplasm is filled with morulae and are in the process of lysis.

FIGS. 10A–10B show identification of *E. equi* in human HL60 cells by PCR of Ehrlichiae species DNA (FIG. 10A), and *E. equi* DNA (FIG. 10B). Ehrlichiae species DNA was amplified using primers PER1 (SEQ ID NO:7) and PER2 (SEQ ID NO:8), and various concentrations of washed *E. equi*-infected HL60 cells (FIG. 10A) as the source of DNA, and revealed the predicted 450 base pair band from as few as 6.25 cells. Using *E. equi*-specific primers GER3 (SEQ ID NO:5) and GER4 (SEQ ID NO:6) in a PCR with DNA obtained from the *E. equi*-infected HL60 cell cultures (FIG. 10B) the predicted 150 base pair fragment was identified. No DNA was amplified from HL60 cells inoculated with uninfected IDE8 tick cells using either set of primers.

DETAILED DESCRIPTION OF THE INVENTION

Figure 1:
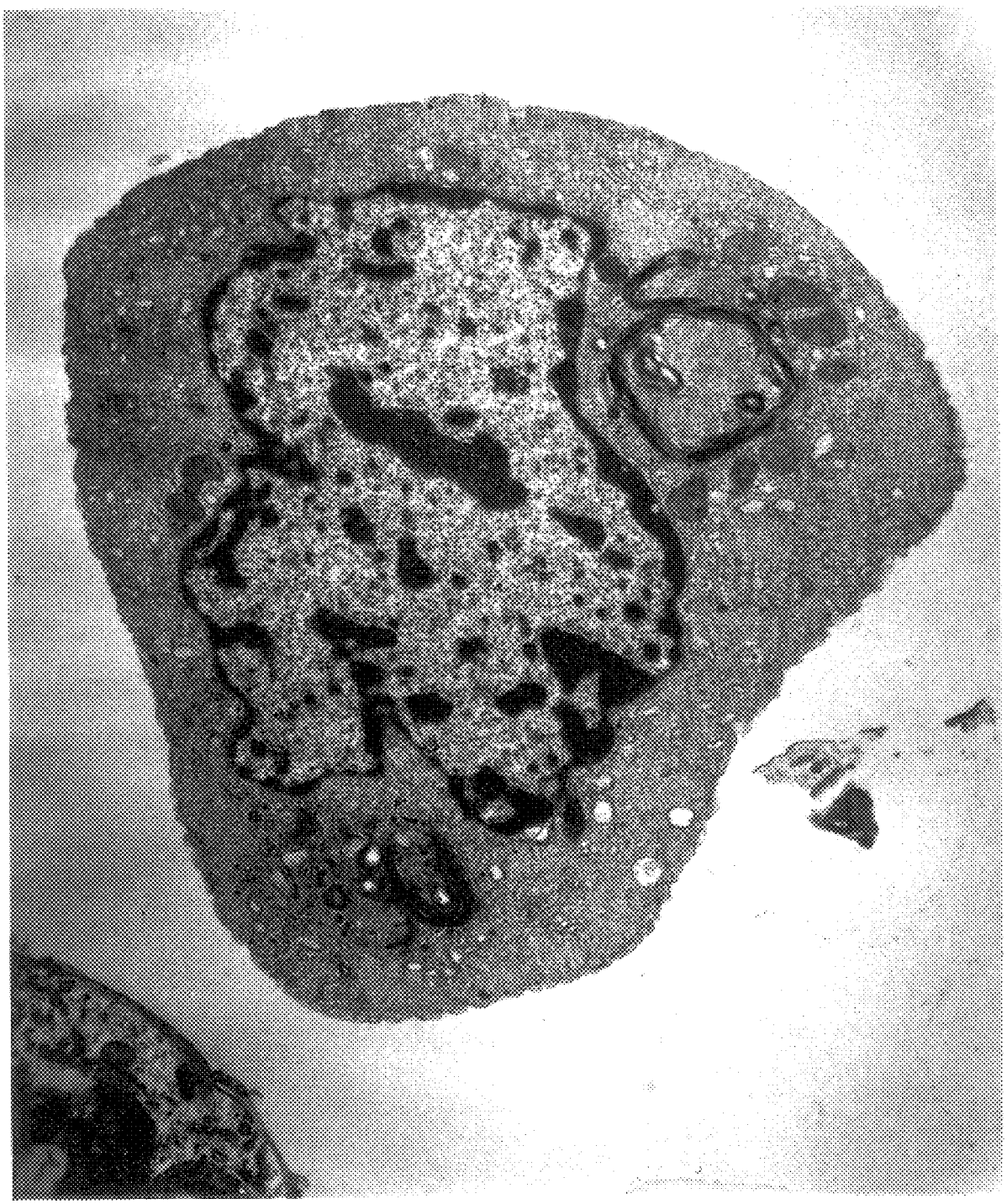

This invention includes methods to culture the obligate intracellular Ep group granulocytic Ehrlichiae in *Ixodes scapularis* tick cell cultures obtained from embryos of the black-legged tick, *I. scapularis*, and in the cultures of the HL60 human promyleocytic leukemia cell line from peripheral blood, which cell line was deposited with the ATCC in 1982 (ATCC No. CCL 240).

Ep group Ehrlichiae have not previously been successfully propagated in continuous cell culture, yet, these bacteria are causes of emerging zoonotic infections of domestic animals and humans. A method of growing Ep group granulocytic Ehrlichiae in vitro is useful to prepare diagnostic reagents, antigen preparations, and vaccine preparations. The method of this invention is useful to grow and/or culture Ep group Ehrlichiae on a large scale, resulting in production of Ehrlichiae containing products at a high yield, and much reduced cost. In addition, large scale in vitro culture eliminates the need to maintain and/or sacrifice *E. equi*-infected horses that can cost in excess of $700.00 for a single horse.

An in vitro culture method in *Ixodes scapularis* cell culture, line IDE8, is also advantageous because Ep group Ehrlichiae can be obtained that are highly purified and free of contamination with mammalian antigens and/or other pathogens. In addition, Ep group products can be obtained that include tick cell antigens that may be advantageous in stimulating a protective immune response. A method to culture the organisms in vitro in tick cells, line IDE8, is particularly advantageous to obtain Ehrlichiae that are free of human or horse antigens, and that do not carry transforming agents, such as tumor viruses or cancer genes. In addition, Ehrlichiae antigens prepared from tick cell cultures may contain tick antigens that can broaden and enhance the immune response and provide a more effective antigen for vaccines. On the other hand, Ehrlichiae prepared in human cell culture can provide antigenic preparations that are particularly suited to serologic diagnosis of the disease in humans and animals.

A. *Ixodes scapularis* Tick Cell Culture

*Ixodes scapularis* tick cell cultures are prepared from embryonic tissues from the tick *I. scapularis*. *Ixodes scapularis* tick cell cultures can be prepared using standard methods as described in Example 1 below. The *I. scapularis* tick is a natural vector for *Borrelia burgdorferi*, *Babesia microti*, and probably *E. equi*, and the synonymous agent of HGE.

*Ixodes scapularis* tick cell culture lines can be established and maintained in vitro. The cells are adherent and can be continually passaged. Several cell lines that are different from one another can be obtained from a single egg mass from one female. Cell lines that are different from one another can also be obtained by using different embryos of different ages. *Ixodes scapularis* cell lines can be characterized using morphology, karyotype and isozyme profile using standard methods as described in Example 1 below.

Several cell lines isolated from *Ixodes scapularis* ticks were obtained from white-tailed deer in Minnesota near the St. Croix River and in Polk County, Wis. These cell lines are designated IDE. The cell lines established from ticks from Minnesota and Wisconsin vary in morphology and isozyme profile. The cell lines are undifferentiated cells, and each cell line can contain more than one cell type.

An example of a tick cell line isolated from ticks from Minnesota and Wisconsin is designated IDE8. IDE8 cells are characterized morphologically by the presence of distinctive fine wavy membrane stacks within vacuoles in the cytoplasm, and have long branching pseudopodia. An electron micrograph of cell line IDE8 is shown in FIG. 1. The cell line is diploid and the modal number of chromosomes is 2n=28 with two sex chromosomes. The IDE8 cells after passage 17 have the following isozyme profile: lactate dehydrogenase isozyme (LDH) with a pI of 6.8 and 7.0 and 7.5; malate dehydrogenase isozyme (MDH) with a pI of 8.5, 8.1, 5.1, 6.1, and 6.7; and malic enzyme (ME) isozyme with pI of 5.1, 5.3, 5.6, 6.2, 6.4 and 6.5. The cells grow firmly attached to the substrate with a population doubling time of approximately 6 days. The IDE8 cell line has been deposited with the American Type Culture Collection in Rockville, Md. on Aug. 26, 1995, under ATCC No. CRL 11973.

*Ixodes scapularis* cell lines are preferably maintained and passaged in a medium that supports the growth of invertebrate cells. The preferred medium is an L15B medium (pH 7.0) (Munderloh et al, *Exp. Appl. Acarology*, 7:219 (1989)). L15B medium is a modification of Leibovitz's L15 medium (Leibovitz, *Am. J. Hyg.*, 78:173–180 (1963)) containing additional glucose, amino acids, vitamins and trace minerals. The complete L15B medium also includes about 80 mM glucose, 10% (w/v) tryptose phosphate broth (Difco Laboratories, Detroit, Mich.), about 3.0–5.0% (v/v) fetal bovine serum (Gibco, Grand Island, N.Y.), and about 0.1% (w/v) bovine lipoprotein concentrate (ICN, Irvine, Calif.). Cell lines are cultured at about 31° C. to 34° C.

Cells can be subcultured at ratios of about 1:3 to about 1:20. The first subculture can be initiated about 6–12 months after primary culture. After establishment of cell lines, cell lines are passaged at about 2 to 3 weeks.

*Ixodes scapularis* cell cultures can also be cultivated using standard large scale culture techniques. These large scale culture techniques include the use of cell factories, bioreactors, hollow fiber tubes and beads. Other culture methods include growing the tick cells in wells or slides or on other readily accessible surfaces.

B. Ep Group Granulocytic Ehrlichiae: *E. equi*, *E. phagocytophila*, and the HGE Agent Ehrlichiae include species that are tick transmitted disease agents. *Ehrlichia equi*, the causative agent of EGE, is tick transmitted, as is *E. phagocytophila*, the causative agent of tick-borne fever of ruminants in Europe. These Ehrlichiae are very closely related to or identical to the newly identified, probably tick-transmitted agent of HGE, which is known to cause a potentially fatal disease in humans. Because of the nearly identical 16S ribosomal RNA gene sequence, strong antigenic similarities, and biological identity, *E. equi*, *E. phagocytophila*, and the agent of HGE, are probably variants of a single species.

In man and animals, these Ehrlichiae infect granulocytic leukocytes, and cause severe febrile diseases that may be associated with decreased host resistance to opportunistic infections. Each of these Ep group granulocytic Ehrlichiae is known or suspected to be transmitted by *Ixodes ricinus* complex (including *I. ricinus* (sheep ticks) in Europe, *I. pacificus* (western black-legged ticks) in California, and *I. scapularis* (deer ticks or eastern black-legged ticks) in the midwestern and eastern United States) ticks. Only those forms that comprise the morulae (the intracytoplasmic clusters of Ehrlichiae organisms) found in mammalian hosts have been investigated and described in some detail. In the neutrophil, Ehrlichiae of the Ep group are always contained within a vacuole of the host cell. Individual Ehrlichiae are described as coccoid to cocco-bacillary in shape, but may be highly pleomorphic. Up to about 20 organisms occupy one morulae in a mammalian leukocyte. The forms that are resident in the vector are not known, and have not been described. Therefore, growing Ep group granulocytic Ehrlichiae in *Ixodes scapularis* cell culture offers the opportunity to analyze and utilize antigens uniquely associated with the vector. Conversely, the availability of the exact same agent in a human cell line provides the chance to study the molecular and cellular interactions of the organism with the human host cells in vitro, and to contrast the two life stages, arthropod and vertebrate, for this organism.

*Ehrlichia equi* obtained from infected horses can be grown in *I. scapularis* tick cell culture. In a method of the invention, Ep group granulocytic Ehrlichiae, such as *E. equi*, are incubated with *I. scapularis* tick cell culture, preferable the IDE8 line. The *E. equi* inoculum can be obtained from horses after experimental inoculation with thawed, *E. equi*-infected blood from an acutely infected horse, followed by venipuncture and removal of fresh, *E. equi*-infected blood at a time when Ehrlichiae are visible in the peripheral blood leukocytes of the ill, infected horse. The organisms found in the neutrophils are always contained within a membrane bound vacuole up to about 3 to 5 μm in diameter. The individual organisms are small, highly pleomorphic, and approximately 0.5 μm in size. With a stain such as Giemsa, Ehrlichiae and the morulae appear bluish-purple. By electron microscopy their electron density is similar to that of the host cytoplasm, but some morulae may additionally contain smaller, dense forms. Buffy coat cells, i.e., all of the white blood cells which collect as a band on top of the packed erythrocytes when blood mixed with an anticoagulant, such as EDTA, is centrifuged, are harvested and washed once in L15B medium. The cell pellet is then added to uninfected IDE8 tick cell cultures, and co-incubated with IDE8 cells.

*Ehrlichia equi* inoculum for propagation in tick cell culture or human cell culture can also be obtained from *E. equi* passaged in tick cell culture. Tick cell cultures in which 10% to about 50% of the cells are infected can be mixed with uninfected tick cells at a ratio of about 1:3 to about 1:20.

*Ehrlichia equi* is cultured in *I. scapularis* cells derived from a suspected natural vector of the pathogen. The requirements for successful isolation of the Ehrlichiae in tick cell culture are: an atmosphere that is reduced in $O_2$ tension (from 20% $O_2$ as found in normal air to about 17%), and enhanced 10-fold with respect to $CO_2$ tension (from 0.03% as found in normal air to about 3%). The culture medium used also must include $CO_2$ in the form of $NaHCO_3$ (0.25% (w/v)), and an organic buffer. An organic buffer, such as 3-(N-morpholino)-propane sulfonic acid (MOPS) or N-(2-hydroxyethyl) piperazine-N-(2-ethanesulfonic acid) (HEPES), at a concentration of 10 to 15 mM is preferably included to ensure growth of *E. equi*. The infected tick cultures are incubated at 31° C. to 35° C. until growth of *E. equi* is detected. Ehrlichia equi grows to high yield in IDE8 cells as compared to neutrophilic granulocytes harvested from horses. Individual cells can contain enormous masses (>1,000) of Ehrlichiae.

This invention also pertains to the preparation of antigens and vaccines derived from tick cell culture.

*Ehrlichia equi* can also be cultured in human HL60 promyelocyte leukemia cells. In a method of the invention, Ep group granulocytic Ehrlichiae, such as *E. equi*, are incubated with log phase growth HL60 cells. The *E. equi* inoculum can be obtained from *E. equi*-infected IDE8 tick cells in which approximately 30% to 50% of the cultured cells contain Ehrlichiae, by Romanowsky staining. Log phase growth HL60 cells are centrifuged and resuspended in tissue culture medium at a concentration of about $3.0 \times 10^6$ cell per ml. The *E. equi*-infected IDE8 cells are then mixed with the HL60 cells, preferably at a ratio of approximately 1:36 (0.25 ml of infected tick cells and 9.0 ml of HL60 cells). The preferred culture conditions include RPMI 1640 medium supplemented with about 10% (v/v) fetal bovine serum (heat-inactivated), about 2.0 mM L-glutamine, and in an atmosphere of 5% $CO_2$ at about 37° C. The co-cultivated cells and HL60 cells are maintained in suspension cultures and are examined periodically, preferably weekly, by Romanowsky staining, for the presence of typical Ehrlichiae morulae indicative of infection. Infected cells may contain single morulae typical in appearance, as seen in the peripheral blood neutrophils of patients with human granulocytic ehrlichiosis, and horses or dogs with *E. equi* granulocytic ehrlichiosis. With progressive time, an increasing percentage of cells become infected, and may contain multiple morulae (see FIGS. 8A–8B), providing an in vitro method to obtain substantial quantities of Ep group Ehrlichiae propagated within mammalian (human) cells.

The IDE8 cells infected with E. equi must be incubated under conditions of reduced $O_2$ and increased $CO_2$ tension. The cells are incubated with an inoculum of infected horse white blood cells for about 2 weeks at 34° C. to 35° C. before growth of E. equi can be detected by light microscopic examination of a cell smear stained, preferably with a Romanowsky-type stain, such as Giemsa or Wright's. Growth of *E. equi* that has been passaged in vitro in IDE8 tick cells is detectable in about one week.

Growth and development of *E. equi* in IDE8 cells and in HL-60 cells can be detected by several methods. One method is to prepare cell spreads using a cytocentrifuge and to stain the cells with Giemsa stain. Infected cells can then be detected by the presence of Ehrlichiae inclusions in the cytoplasm. The inclusions seen in HL-60 cells are similar to those seen in vivo in the neutrophilic granulocytes of humans, dogs and horses. The inclusions in *I. scapularis* cell cultures are much different, in particular, they are much larger and more densely packed with organisms. Inclusions in heavily infected cells can completely fill the cytoplasm, and cause the cell to become distended. Such cells may increase to more than 50 μm in diameter. Ehrlichiae in IDE8 tick cell culture are very pleomorphic, and either stain pale purple or intensely deep purple.

Alternatively, growth can be detected by immunocytological methods using specific *E. equi, E. phagocytophila*, or HGE agent antibodies in indirect fluorescent antibody methods and indirect immunoenzymatic methods (see FIGS. 7A–7F and FIG. 9).

*Ehrlichia equi* infection in vitro can also be detected by PCR using primers designed specifically to amplify only Ep group DNA. PCR can be conducted on isolated whole *E. equi*-infected cell culture DNA. Primers can be designed based upon the DNA sequence of the 16S ribosomal RNA gene in regions conserved among *E. equi, E. phagocytophila*, and the HGE agent. Primers are typically complementary to and/or hybridize to a 5' region and a 3' region of the nucleic acid sequence. Primers preferably have at least 15 nucleotides that are 100% complementary to the nucleic acid sequence. Primers are preferably about 15 to 50 nucleotides long and can be prepared by automated synthesis.

The preferred primers amplify a 919 base pair fragment of the Ep group 16S ribosomal RNA gene and have the following sequences (Chen et al, supra): ge9f 5'-AACGGATTATTCTTTATAGCTTGCT-3' (SEQ ID NO:1) ge10r 5'-GGAGATTAGATCCTTCTTAACGGAA-3' (SEQ ID NO:2); or a 928 base pair fragment of the Ep group 16S ribosomal RNA gene and have the following sequences: EE3 5'-GTCGAACGGATTATTCTTTATAGCTTGC-3' (SEQ ID NO:3), EE4 5'-CCCTTCCGTTAAGAAGGATCTAATCTCC-3' (SEQ ID NO:4), PCR can be conducted as described in Example 3 below.

Alternately, the following primers can be constructed to specifically amplify a 150 bp DNA fragment from *E. equi* and Ep group Ehrlichiae. Examples of such primers include: GER3 5'-TAGATCCTTCTTAACGGAAGGGCG-3' (SEQ ID NO:5) GER4 5'-AAGTGCCCGGCTTAACCCGCTGGC-3' (SEQ ID NO:6). These primers can also be used to detect the presence of Ep group Ehrlichiae in infected cell cultures such as *E. equi*-infected HL60 cell cultures.

Species within the genus Ehrlichiae can be identified by PCR using primers, such as: PER1 5'-TTTATCGCTATTAGATGAGCCTATG-3' (SEQ ID NO:7) PER2 5'-CTCTACACTAGGAATTCCGCTAT-3' (SEQ ID NO:8)

Development of *E. equi* can also be assessed by electron microscopy. Growth of *E. equi* in IDE8 tick cells results in the development of many intracytoplasmic vacuoles that contain from one to more than 40 individual Ehrlichiae. An infected cell may have one or many inclusions (morulae). The Ehrlichiae have the typical ultrastructural features of *E. equi*, the human granulocytic Ehrlichiae, and other Ehrlichiae species (Sells et al, *Infect. Immun.,* 13:273 (1976); Bakken, supra; and Chen, supra) including variable size (0.2 to 3.0 μm in maximum length), variable shape (coccoid to coccobacillary to irregularly contoured organisms), that have typical thin outer and inner cell envelopes. The Ehrlichiae have chromatin and ribosomes as seen in other bacteria; however, two distinct morphologic forms may be identified within one vacuole; one form, the dense core form, has densely-packed chromatin, while the other, i.e., the reticulate core form, has more dispersed chromatin. Many of the Ehrlichiae are invested with apparently redundant membrane, resulting in the appearance of intravacuolar tubules, vesicles, and occasional organisms that have multiple membrane layers.

Growth of *E. equi* in HL60 cells causes a progressive appearance of morulae in an increasing percentage of HL60 cells over time. After 4 weeks of cultivation, cell clumping of HL60 cells was detected, and after 7 weeks of cultivation, many cells were in the process of lysis with release of individual Ehrlichiae into the supernatant medium. In *I. scapularis* tick cell culture maximally 50% to 60% of the cells become infected. At that point, tick cells lyse and degenerate after the formation of large inclusions and multiple, repeated invasions.

The invention also includes tick cell cultures and human HL60 promyelocytic leukemia cells infected with *E. equi*. The infected tick cell and human cell cultures are useful as diagnostic tools for assays including ELISA, indirect fluorescent antibody tests, latex agglutination tests, complement fixation tests, and immunoblot tests. It is preferred that 100 to 1000 cells be present on a slide with about 50% to 100%, and no less than 25% of cells infected.

Infected IDE8 tick cell cultures can be grown on slides, in wells and on other readily accessible surfaces. Infected tick cell cultures can also be grown using large scale cultivation techniques as described above. It is believed that because of an increase in the number of microorganisms present per infected cultured tick and human HL60 cells, as well as the number of infected tick cells compared with equine granulocytes, a great enhancement in yield and reproducible quality of antigen can be obtained at a much lower cost. Many infected tick cells contain large inclusion bodies with multiple individual Ehrlichiae compared with smaller inclusions with fewer individual Ehrlichiae per infected equine granulocyte.

In addition, the ability to grow infected tick cells on a large scale can provide for a further enhancement in yield at a much lower cost. An infected horse yields about 2.0 l of infected blood containing about $1.2\times10^6$ infected granulocytes per l. An infected horse costs approximately $700.00 to initiate infection, and to maintain the animal during the course of infection and convalescence. The animal can only be infected once, and new horses must continually be available. Moreover, biological variation among animals yields varied, and unpredictable levels of ehrlichemia and lack of reproducibility in *E. equi* antigen production. Thus, the tick cell culture allows for reproducible, high quality, low cost production of Ehrlichiae for antigen preparation and vaccine preparation.

Vaccine preparations can include whole microorganisms, antigen preparations, and/or subunit vaccines. The vaccines can be heat-killed or live attenuated microorganisms. Vaccine formulations can be prepared in accordance with methods standard in the art.

Preferably, heat-killed vaccines and antigen preparations of Ep group granulocytic Ehrlichiae are made from Ep group granulocytic Ehrlichiae passaged in *I. scapularis* tick cell culture from about 4 to 6 weeks, and that retain infectivity for horses. *E. equi* passaged in tick cells at 3 passages retains infectivity for horses. The infectivity of passaged *E. equi* can be determined in horses by standard methods as described in Example 4 below.

Preferably, the vaccine and antigen preparations are essentially free of horse antigens and/or other pathogens. Vaccine and antigen preparations from infected horses can be contaminated with horse antigens that can result in a formation of an immune response to the horse antigens. This immune response to horse antigens can cause adverse immunological responses in vaccinees. Contamination of horse blood with other pathogens may also occur since large amounts of blood are necessary to prepare vaccines and/or antigen preparations.

In contrast, Ep group granulocytic Ehrlichiae grown in tick cell culture can be produced on a large scale with little or no contamination with horse antigens or other equine pathogens. Electron micrographs of infected cultures indicate that contamination with horse pathogens has not been detected. Because only a small amount of horse blood is used as inoculum, and *E. equi* can be passaged several times, costly separation of the *E. equi* antigens from dog cells and contaminants can be avoided.

The vaccine and antigen preparations can also include *I. scapularis* tick cell antigens. The presence of *I. scapularis* tick cell antigens may provide an additional protective immune response. Optionally, the vaccine and/or antigen preparations can be further purified from tick cell antigens using antibodies specific for *E. equi* and methods known to those of skill in the art.

Heat-killed *E. equi* and/or antigen preparations are combined with physiologically acceptable carriers to form vaccines. The physiologically acceptable carriers include buffered salt solutions, phosphate buffered saline, and cell culture medium. Optionally, the vaccine formulations can include adjuvants, such as alum, IPSCOMS, complete Freund's adjuvant, incomplete Freund's adjuvant, and saponin.

The vaccines are administered by a variety of routes including intravenous, intraperitoneal, intramuscular, intradermal and subcutaneous. The preferred route of administration is intramuscular. The vaccine can be administered in a single dose or multiple doses until a protective effect is achieved. It is preferred that the vaccine stimulate a protective immune response to infection with Ep group granulocytic Ehrlichiae. It is also preferred that the vaccine ameliorate and/or prevent the development of the symptoms of granulocytic ehrlichiosis.

Antigen preparations are also useful to prepare diagnostic tools, such as ELISA plates, latex agglutination, solid phase immunoassays, complement fixation tests and the like. Antigen preparations can be prepared from the Ep group granulocytic Ehrlichiae grown in *I. scapularis* tick cell culture as described in Example 5 below and by standard methods. Alternately, to obtain an antigen preparation of Ep group granulocytic Ehrlichiae propagated in mammalian cells and likely to express antigens that react with antibodies produced after mammalian infection, the HL60 human promyelocytic leukemia cell line is used as described in Example 6 below, and by standard methods.

In a preferred version for preparation of tick phase Ehrlichiae, *E. equi* from infected equine blood is cultured in cell line IDE8 at about 34° C. to 35° C. *Ehrlichia equi* is cultured with the tick cells in L15B medium supplemented with 10 to 15 mM MOPS, and a source of $HCO_3$. The cells are incubated in 17% oxygen and 3% $CO_2$. The cells are incubated a sufficient time to achieve a 70% to 100% rate of infected cells, and then are incubated with uninfected tick cells at a ratio of 1:3 to 1:5. After about 4 to 6 passages (approximately 4 to 6 weeks) the *E. equi* are harvested as described in Example 3 below, and used as antigen or vaccine.

In the preferred version for preparation of mammalian phase Ehrlichiae, *E. equi*-infected IDE8 tick cells in which 10% to 50% of cells are infected are cultured with the HL60 cells in RMPI 1640 medium containing 10% (v/v) fetal bovine serum, 10 mM HEPES buffer, 2.0 mM L-glutamine in an environment of 5% $CO_2$ at 37° C. After about 21 days, morulae are detectable by Romanowsky staining, and by day 49, 27% of the HL60 cells contained *E. equi* morulae. The infected HL60 cells may then be harvested as described in Example 6 below, and used for antigen preparation or as a source from which to purified Ep group granulocytic Ehrlichiae for vaccines.

Antigens for diagnostic serologic tests are preferably prepared by harvesting sufficient quantities of infected *I. scapularis* IDE8 tick cells or HL60 cells when approximately 50% or more of the cultured cells contain Ep group Ehrlichiae. The antigens may be used directly as fixed whole infected cells for indirect fluorescent antibody tests or may be purified by density-gradient centrifugation of lysed, infected tick cell cultures for latex agglutination, ELISA, solid phase enzyme immunoassay, or immunblots.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The following examples are provided for illustrative purposes only and are in no way intended to limit the scope of the present invention.

EXAMPLE 1

Establishment, Maintenance and Description of Cell Lines from *Ixodes Scapularis*

Cell lines were established from embryonic tick cell cultures. Cell lines were maintained and characterized.

A. Ticks

Engorged female black-legged ticks (*I. scapularis*) were collected from hunter-killed white-tailed deer (*Odocoileus virginianus*) in Minnesota near the St. Croix River and in Polk County, Wis. They were surface-disinfected as described by Kurtti et al, *J. Parisitol.,* 69:1072 (1983), and individually placed into wells of a sterile 12-well cell culture plate. Plates were held in a desiccator over sterile distilled water under a 16-hr light/8-hr dark program at 25° C. during light, and 20° C. during dark periods. The onset of oviposition was recorded for each tick, and used to determine the age of the embryos, i.e., age in days post-onset of oviposition (days po). Embryos from these ticks were used to establish cell lines coded "IDE".

Gravid southern black-legged tick females (*I. scapularis*) were obtained from Dr. J. H. Oliver, Jr. (Georgia Southern University, Statesboro, Ga.). They were surface disinfected, and held for oviposition as described above. Embryos from these ticks were the source material for cell lines coded "ISE".

B. Primary Cultures

Nunc plasticware (Nunc, Roskilde, Denmark) was used throughout this study. The 25 $cm^2$, 50 ml volume flasks provided a ratio of air space to medium volume that was favorable to tick cell growth, and the screw caps did not crack during the many months until primary cultures were subcultured for the first time.

Twenty-three to 27 days po, egg masses were separately scooped into sterile 35 mm diameter plastic Petri dishes and weighed. The eggs were gently crushed in 0.5 ml of L15B medium (Munderloh et al, supra), about pH 7.0, containing 80 mM glucose, and supplemented with 10% (w/v) tryptose phosphate broth (TPB; Difco Laboratories, Detroit, Mich.), 20% (v/v) heat-inactivated fetal bovine serum (FBS; GIBCO, Grand Island, N.Y.), 100 units/ml penicillin and 100 μg/ml streptomycin (GIBCO). This medium is hereinafter referred to as "primary culture medium". Tissues and egg shells were resuspended in 10 ml of the same medium, and centrifuged once at 100×g. Pellets from egg masses weighing 40 mg or more were divided into 2 fractions that were separately seeded into 25 $cm^2$ flasks in 5.0 ml of primary culture medium. The top layer contained most of the egg shells, but also a substantial amount of embryonic tissues. The bottom layer contained the majority of the tissue fragments and only a few shells. Pellets from smaller egg masses were not subdivided, but transferred to a single 25 $cm^2$ flask. Neither culture flasks nor media were "conditioned" (Yunker, In: *Arboviruses in Arthropod Cells*, CRC Press, Vol. 1, pages 35–37 (1987)) prior to use. Primary cultures were coded "IDE" or "ISE", as appropriate, followed by a number and incubated at 31° C.

C. Establishment of Cell Lines

All cultures were fed 1 week after initiation by replacing 4.0 ml of the primary culture medium with 5.0 ml of fresh primary culture medium. Thereafter, cultures were fed once a week with 5.0 ml of fresh primary cultures medium. The first subculture was carried out 6–12 months after initiation of the primary culture. The antibiotics were omitted, the concentration of serum in the medium was reduced to 5.0% (v/v), and 0.1% (w/v) of bovine lipoprotein concentrate (ICN, Irvine, Calif.) was included (complete medium, pH 7.0–7.2). Attached cells were resuspended in fresh complete medium by using a 14 gauge, 10 cm laboratory cannula (Becton Dickinson, Oxnard, Calif.) with bent tip fitted to a 5.0 ml LuerLok syringe. One-half of the cell suspension was transferred to a new 25 $cm^2$ flask, and the medium volume in both the parent and the daughter cultures brought back to 6.0 ml. Subsequently, 2 subcultures were initiated from each parent culture by transferring one-third (equivalent to a subculture ratio of 1 to 5) of the cell suspension to a new flask, leaving approximately one-half in the parent culture. Cultures in which the cells multiplied to cover 90% or more of the culture substrate (confluency) within 2 weeks after subculturing were also subcultured, and photographed using a inverted phase-contrast microscope.

D. Staining for Ehrlichiae Agents

To test cell lines for the presence of rickettsiae and Ehrlichiae agents, cell cultures were resuspended at a concentration of $5.0 \times 10^4$ cells/ml, and 0.5 ml volumes centrifuged onto microscope slides using a Cytospin (Shandon Southern Instruments, Sewickley, Pa.) at 60×g for 10 min. The preparations were heat-fixed, and immediately stained with Gimenez (1964) stain, or fixed twice in absolute methanol and stained for 30 min at 37° C. in 6.0% (w/v) Giemsa's stain in Sorensen's phosphate buffer (pH 6.5). Stained slides were examined using a magnification of x 1,000.

For immunofluorescence microscopy, the slides were double-fixed in methanol, overlaid with rabbit antiserum directed against spotted fever group rickettsiae (obtained from Dr. R. A. Heinzen, Rocky Mountain Laboratories, Hamilton, Mont.), diluted 100-fold in phosphate-buffered saline (PBS) (pH 7.2), and incubated for 30 min at 37° C. in a humid atmosphere. The preparations were then rinsed in sterile $H_2O$, immersed for 10 min in PBS with 3.0% (w/v) bovine serum albumin (BSA) (pH 7.2), and incubated for 30 min with fluorescein-isothiocyanate-labeled goat anti-rabbit IgG (Sigma, St. Louis, Mo.). The slides were rinsed in PBS, mounted in PBS with 3.0% (w/v) BSA and 10% (v/v) glycerol, and viewed under UV light illumination using a microscope equipped for epifluorescence.

E. Cryopreservation

From the first subculture, cell lines were periodically frozen in liquid nitrogen using a Union Carbide Freezing Tray (Indianapolis, Ind.) and a 35 VHC liquid nitrogen tank (Taylor Wharton Cryogenics, Theodore, Ala.). The setting of the device that yielded a temperature drop of 1° C. per min was determined as follows: the level of nitrogen in the tank was measured from the center using a dip stick marked at 1 cm intervals. A small hole was drilled into the cap of a 1.8 ml capacity plastic freezing tube with a "male" screw cap. The tube was filled with 1.5 ml of freezing medium prepared by adding 10% (v/v) dimethyl sulfoxide (DMSO) to complete medium with 20% (v/v) FBS, and a thermocouple inserted through the cap into the medium. This and 5 additional tubes containing freezing medium were placed into the stage of the freezing tray adjusted to the highest position, and inserted into the neck of the nitrogen tank. Every 10 min, the temperature was recorded using a Bailey cryothermometer (Bailey Instruments Co., Saddle Brook, N.J.) until a temperature of −60° C. was reached. These measurements were repeated for each setting of the tray (settings 1–6), and for several levels of nitrogen in the tank (between approximately 15 cm and 30 cm). At about −25° C., i.e., 45 min after beginning the freezing process, a brief rise in temperature occurred; this was dampened by lowering the freezing stage by 2.5 cm at that time. The derived data were tabulated and used to determine the appropriate conditions for freezing cells.

For each 25 cm flask of cells to be frozen, 1.5 ml of freezing medium was prepared. When the exothermic reaction had subsided, the cultures were resuspended in freezing medium, and 1.5 ml of cell suspension placed into freezing tubes. Tubes were evenly spaced in the freezing tray adjusted to a position appropriate for the amount of nitrogen and the number of tubes. After 45 min, the crank was turned to lower the stage by 2.5 cm. The tubes were transferred into the liquid or vapor phase of nitrogen after a second period of at least 45 min.

To test the viability of each batch, a tube of cells was regenerated after 1 week by quickly thawing it in a 37° C. water bath, and adding the suspension to a 25 $cm^2$ flask in 5.0 ml of complete culture medium containing 50 μg gentamicin/ml. The supernatant was replaced with complete culture medium, and gentamicin was omitted after 1 week. Alternatively, freshly fed cultures could be held for several weeks to months at 12° C.

F. Karyotyping

To determine the diploid chromosome number for each cell line, cultures were treated overnight at 34° C. with 0.1 mg/ml of colcmid (GIBCO). The cells were then swelled in hypotonic saline, fixed in a mixture of glacial acetic acid and methanol, and dropped onto wet microscope slides (Nichols et al, *Current Topics in Microbiol Immunology,* 55:61 (1971)). Chromosomes were stained in 10% (w/v) Giemsa's stain, and the modal number and distribution determined by evaluating 100 metaphase sets.

G. Isoelectric Focusing of Enzymes

Cells were washed twice in $Ca^{2+}$-, $Mg^{2+}$-free Dulbecco's phosphate-buffered saline (DPBS), resuspended in DPBS and centrifuged at 275×g at 4° C. for 10 min. The pellets were lysed in an equal volume of a 1.0% (w/v) glycine solution and stored at −20° C. The internal organs from 5 unfed northern female *I. scapularis* ticks were pooled, and extracted in the same manner. For comparison, extracts of line RAE25 (Munderloh et al, supra) from *R. appendiculatus* were run on the same gels. Extracts were clarified by centrifugation at 15,600×g for 15 min at 4° C., and were applied to squares of filter paper (5–10 ml/25 mm) placed on the gel approximately 10 mm from the anode. Ampholytes (Ampholine (pH 3.5–9.5) from sigma, or a mixture of 3 ampholytes (pH 2.7–5, pH 5–7, and pH 8–10) from BioRad, Hercules, Calif.) were incorporated into native polyacrylamide gels (8.0% (w/v) total polyacrylamide concentration, with 3.0% (w/v) bisacrylamide as the cross-linker) as directed by the manufacturer. Three isozymes were analyzed: lactate dehydrogenase (LDH, EC 1.1.1.27), malate dehydrogenase (MDH, EC 1.1.1.37), and malic enzyme (ME, EC 1.1.1.40). For LDH and MDH, Ampholine (Sigma) was used, but the mixed ampholytes from BioRad were used to resolve ME. Bands were focused to equilibrium in a BioRad model 111 mini isoelectric focusing (IEF) cell at 4° C. in a 3-stage program for 15 min at 100 V, another 15 min at 200 V, followed by 450 V for 1 hr, as specified by the manufacturer.

Enzyme bands were visualized by incubating gels in the appropriate tetrazolium-based staining solution until bands were sufficiently developed as described by Pasteur et al, *Practical Isoenzyme Genetics,* Ellis Horwood, Ltd. (1988).

For LDH staining, the gels were incubated in the dark in a solution containing 1.0 ml of nicotinamide adenine dinucleotide ($NAD^+$, 1.0% (w/v) in $H_2O$), 6.0 ml of 0.5 M lithium D-L-lactate, and 35 ml of 0.2 M tris(hydroxymethyl) aminomethane-HCl (pH 8.0) (TRIS-A). Just before use, a 1.0% (w/v) aqueous solution of nitroblue tetrazolium (NBT, 0.3 ml) and a 1.0% (w/v) aqueous solution of phenazine methosulfate (PMS) were added. When dark blue bands appeared, the gels were washed in deionized water and fixed in absolute methanol.

For MDH staining, the gels were immersed in a solution made of 2.0 ml $NAD^+$(1.0% (w/v)), 0.3 ml 0.5 M $MgCl_2$, 5.0 ml 2.0 M malic acid (pH 7.0), and 35 ml TRIS-A. Nitroblue tetrazolium (0.3 ml) and 0.5 ml PMS were added immediately prior to use. The gels were incubated for 30–60 min in the dark until a dark blue band appeared, then washed and fixed as stated for LDH.

To stain ME, the following components were mixed together: 0.1 ml nicotinamide adenine dinucleotide phosphate ($NADP^+$), 1.0 ml 2.0 M malic acid (pH 7.0), 1.5 ml 0.5 M $MgCl_2$, and 10 ml TRIS-A. Phenazine methosulfate (0.1 ml, 1.0% (w/v)), 0.3 ml NBT (1.0% (w/v)), and thiazolyl blue (MTT, 1.0% (w/v)) were added freshly. This solution was brushed on to the gel, and the gel incubated in the dark for 30–60 min. The gel was then washed and fixed as stated above. The distance of migration of isozyme bands in air-dried gels was measured from the anode.

Eight proteins with known isoelectric point (pI) values ranging from 4.65 to 9.6 (BioRad) were resolved under nondenaturing conditions in polyacrylamide gels, as described above, using Sigma's ampholine (range 3.5–10), or the ampholyte mixture from BioRad. The running conditions were identical to those used for the cell extracts. The gels were fixed and stained with BioRad's silver stain kit. To determine the pI values of unknown isozymes, bands in the cell extracts were compared with the known protein in a "standard" gel employing the appropriate ampholyte. Extracts from cell lines (kept separate by subculture number), or female ticks were run at least 3 times in different gels, and the values calculated for each band were averaged.

H. Results

The egg masses from feral northern black-legged ticks weighed 77 mg on average (range: 19–147 mg), and those from southern females ticks weighed on average 102 mg (range: 59–147 mg). The embryos were used at an age of 23–27 days po. All cultures from egg masses of feral ticks remained clean, but 10 of 17 from laboratory-raised females became contaminated within 10 days with antibiotic-resistant bacteria. Contaminated cultures were discarded. All feral egg masses were fertile, but one of the laboratory-raised females laid an unfertilized batch of eggs weighing 122 mg. Only egg masses that weighed at least 90 mg gave rise to successful primary cultures with the exception of one egg mass weighing 66 mg (embryo age: 25 days po). Cultures with low cell numbers could be "rescued" by pooling cells from 2 to 6 flasks as appropriate. Cells in pooled cultures subsequently resumed growth and developed into established lines.

Attachment of single, hemocyte-like cells was detected within several hours of seeding. Fragments of gut and Malpighian tubules were recognized by their microscopic appearance, active contractility, and the presence of guanine granules in the latter. Leg fragments were identifiable by the presence of epidermal structures, such as cuticle and claws. Central ganglia with nerve trunks attached were present as well. These tissues remained nonadherent at first but later, within a week to a month, became anchored to the culture substrate with cells migrating from the torn or broken ends. Multicellular, hollow spheres (vesicles) frequently grew from hollow organs from which they eventually detached. Such structures (i.e., vesicles) have been described in many invertebrate cell lines.

The time interval between initiation of the primary culture and when the first subculture was made ranged from about 6 months to 12 months. Cultures from large inocula resulted in a more diverse mixture of cells than those that were seeded with tissues from fewer eggs, or with the egg shell fraction. Line IDE1 grew loosely attached to the substrate as clumps of small round cells mixed with a few larger ones. Line IDE2 contained firmly adherent cells, as well as others that were refractive and round. Line IDE8 cells characteristically had very long (30–40 nm or more), often branching, pseudopodia and resembled neuronal cells. IDE12 cells had the appearance of plasmatocytes in Wright-stained smears. Cell line ISE5 contained the most diverse cell types. Long, bipolar cells with a foamy cytoplasm were common, and grew between clumps of round cells and adherent vesicles. While myoblasts were present in all young lines, pulsating myotube-like structures were more common in ISE5. Line ISE18 cells also tended to form muscle, but here large patches of flattened cells twitched and shifted in an unorganized fashion. Differentiated muscle tissue rarely formed in more highly passaged cell lines (>10 subcultures). With subculturing, the number and diversity of cell types in a line declined, and 1 or 2 cell types became dominant. This was shown by comparing the longer-established IDE lines, particularly IDE1, with the younger ISE lines. Attempts to clone any tick cell lines either by limiting dilution or soft-agar cloning were unsuccessful. Subcultures were done every 2–4 weeks by diluting the cell suspension 5–10-fold. The cells reattached within a few hours of postseeding.

A representative electron micrograph is shown in FIG. 1. In FIG. 1, an electron micrograph of cell line IDE8 is shown. The IDE8 cells have characteristic stacks of fine wavy material resembling strands of hair.

Cells thawed from liquid nitrogen storage were successfully re-established in culture.

There was no evidence for the presence of rickettsiae agents found in the cell lines by staining with Giemsa's or Gimenez (1964) stain, or by indirect immunofluorescent antibody testing.

Figure 2:
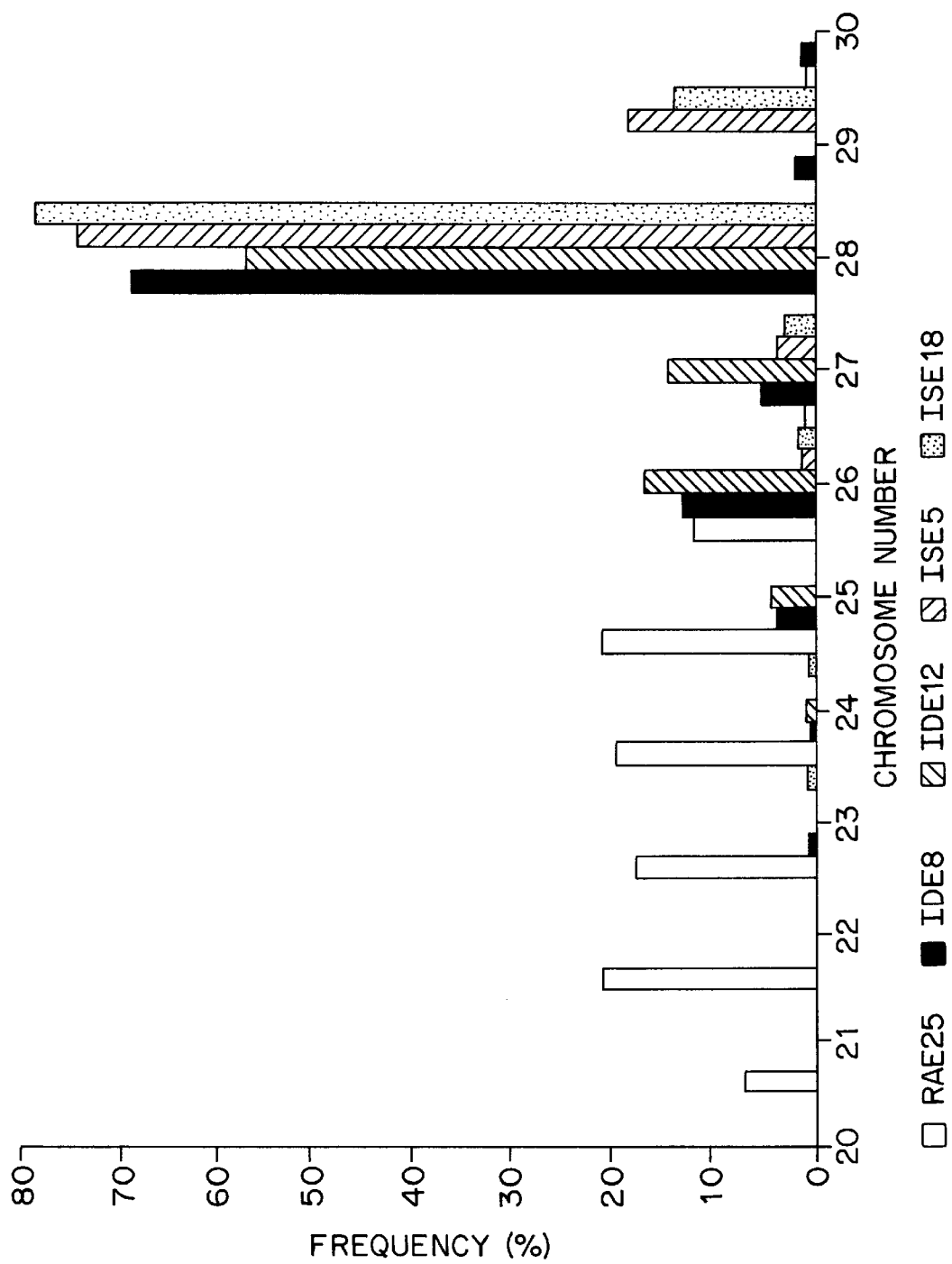

As shown in FIG. 2, all of the cell lines were predominantly diploid, and the modal number of chromosomes (28), and their general morphology, conformed to that reported for *I. scapularis* by Oliver et al, *J. Med. Entomol.,* 30:54 (1993). By comparison, the highly passaged cell line RAE25 had about equal numbers of sets with 22–25 chromosomes, and approximately 10% of the sets had 21 and 26 chromosomes, respectively. *Rhipicephalus appendiculatus* has an XX/XO sex-determining system with 2n=22 in female and 21 in male ticks (Wysoki et al, *Genetica,* 48:233 (1978)).

Figure 3A:
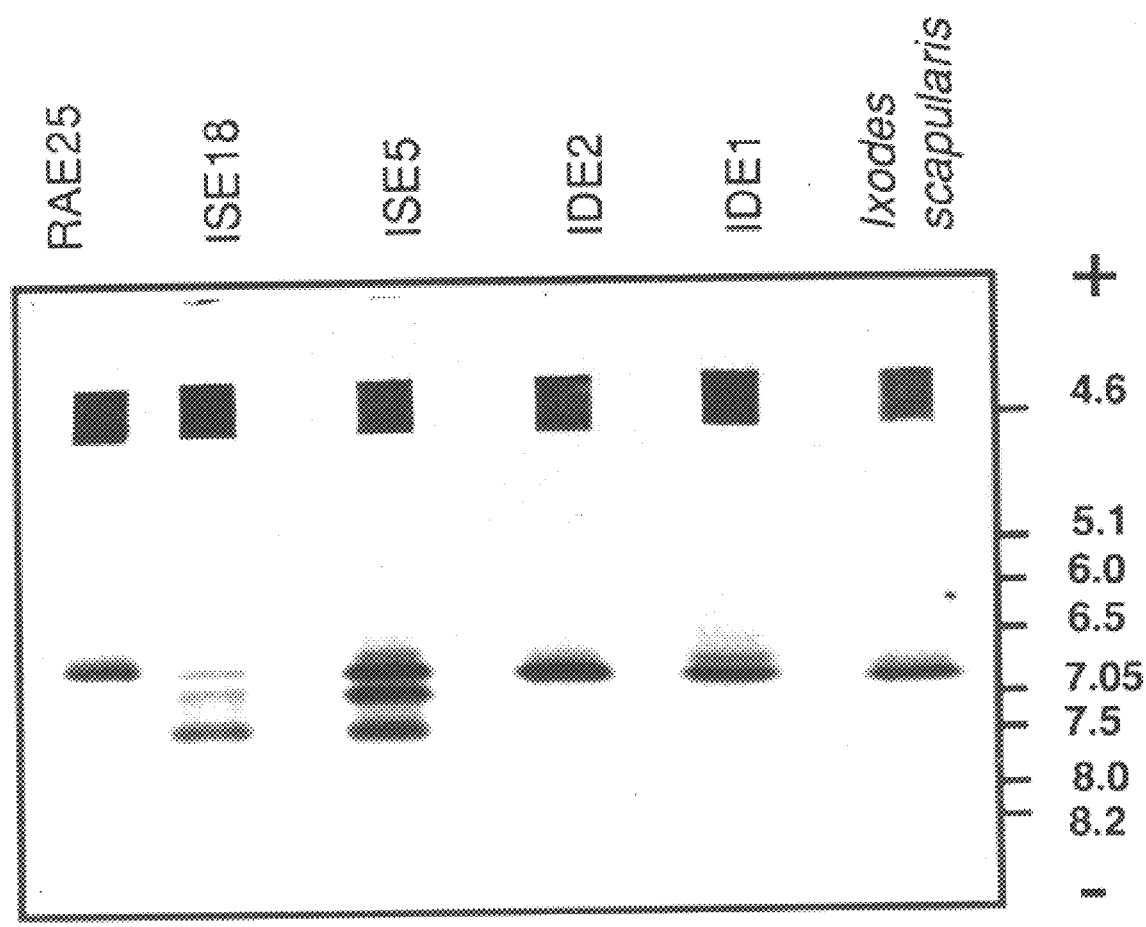

As shown in FIG. 3A, LDH was readily stainable in extracts from all of the cell lines. All of the IDE lines showed one major band with a pI value of 6.8. In line ISE5, there were two additional, consistent major bands with pI values of 7.0 and 7.5, respectively. In ISE18, the same three bands were present in early subculture (<10) cell extracts; but, in cells that had been in culture longer, the two bands with the lower pIs diminished in intensity, leaving only the isozyme with a pI of 7.5. Extracts from tick tissues displayed a single major band that corresponded to that in the majority of the cell lines (pI=6.8). RAE25 cells also had only one band that consistently focused at a slightly more acidic pH (pI=6.7) than IDE and ISE extracts.

Figure 3B:
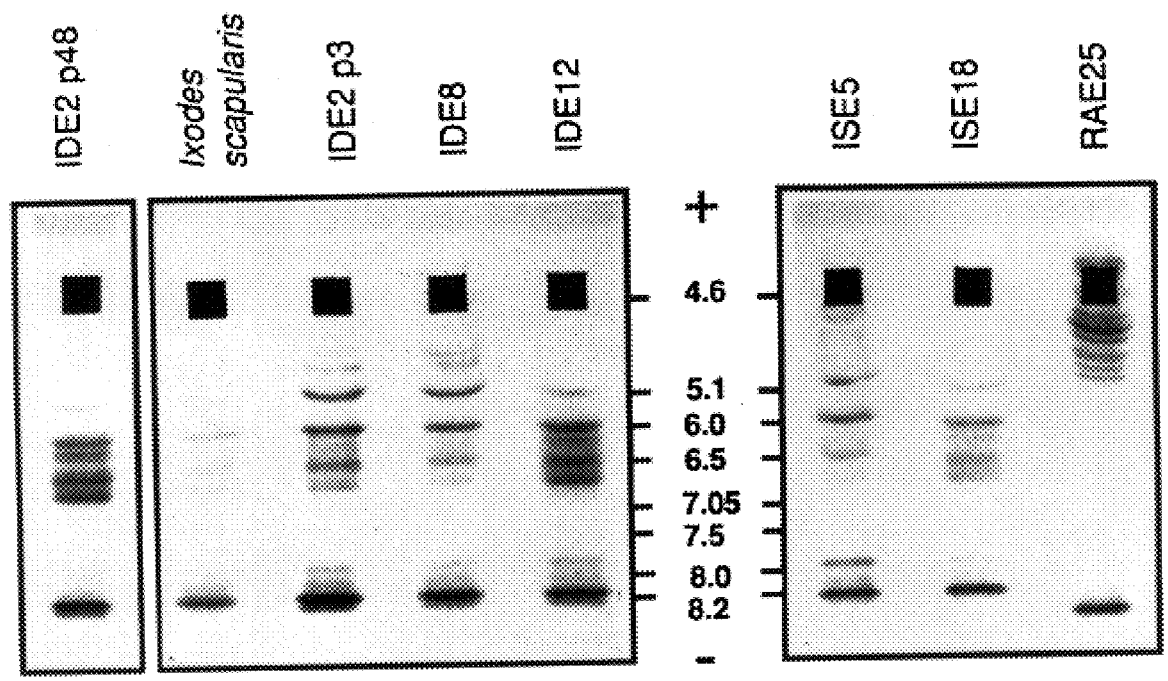

As shown in FIG. 3B, in Ixodes cell lines and extracts from female northern black-legged ticks, the MDH staining pattern was more complex. The most prominent band was an enzyme focusing at pH 8.5. This was accompanied by a minor band equilibriating at pH 8.1, which was very intense in ISE5. In addition, there were four lesser bands with mildly acidic to neutral pI values of 5.1, 6.1, 6.7, and 6.9. The last band was distinct in IDE12 and IDE2, but weak in the other cell lines, whereas at higher passage numbers (>30) the isozyme band with a pI value of 5.1 diminished. In comparison, the *R. appendiculatus* line RAE25 had one enzyme species with a pI value near 9, and four-five inconsistent minor bands with pIs between 4 and 5.

Figure 4:
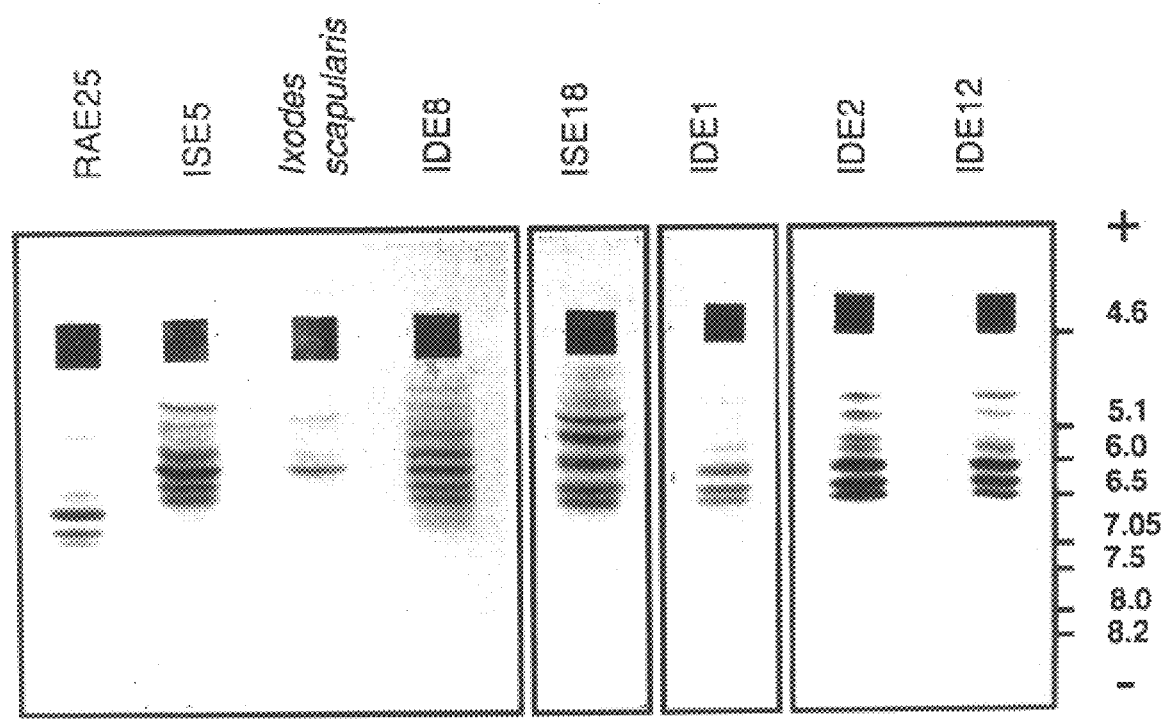

As shown in FIG. 4, in Ixodes cells, the ME staining pattern did not include any alkaline isozymes, and all bands focused between pH 5.0 and 6.5. There were three major bands that focused at pH 6.2, 6.4, and 6.5. In addition, there was a weak, but consistent band with a pI value of 5.1, followed by two stronger isozymes with pIs of 5.3 and 5.6, which were most evident in ISE18 and less intense in IDE12 and IDE2. Tick tissue extracts had rather weak ME activity, showing the major band at pH 6.0, and a minor band at pH 5.1. RAE25 cells displayed a major band that focused at pH 6.5, followed by one or two bands with pI values of 6.7 and 6.8. An additional minor, but distinct isozyme focused at pH 5.5.

LDH, MDH and ME yielded the most consistent results. The pattern of minor and major MDH bands allowed distinction between the genera Ixodes and Rhipicephalus, but not between Ixodes lines. LDH gave the most consistent banding pattern, and discriminated between IDE lines and ISE5 and ISE18. In other species, e.g., mosquitoes, LDH is known to be a tetramer and must be in its tetrameric form in order to function (Pasteur et al, supra). The fact that ISES showed three major LDH bands, and most other Ixodes-cell lines showed one band, may indicate that in *I. scapularis,* LDH is a dimer. Both dehydrogenases were found to be useful for distinguishing Ixodes cell lines from cell line RAE25. Although ME showed a similar pattern in all cell lines examined, two distinct minor bands (pI of 6.7 and 6.8) were found only in RAE25.

Degradation of $NADP^+$ can generate enough $NAD^+$ to reveal MDH activity in gels stained for ME. Thus, it is conceivable that those bands in the ME gels that focused at a similar pH as some of the MDH bands actually represented MDH. However, a band analogous to the most intensely staining MDH band with a pI of 8.5 never appeared in ME gels, arguing against $NAD^+$ contamination. Furthermore, NADP was either prepared fresh or stored frozen to guard against degradation. The enzyme activities and banding patterns of the Ixodes cell lines were consistent with the data obtained from tick tissue extracts, confirming their species identity. While karyotype analyses also confirmed the cell lines to be of Ixodes origin, this technique did not detect differences between cell lines.

Tick cell culture IDE8 was deposited on Aug. 24, 1995, with the American Type Culture Collection in Rockville, Md. under ATCC No. CRL 11973. Tick cell culture IDE8 has the following characteristics: The cells grow firmly attached to the substrate with a population doubling time of approximately 6 days. They are primarily round, particularly at high cell density, but may form long pseudopodia. They have a unique ultrastructural feature, i.e., they have folded membrane stacks with vacuoles. The modal chromosome number is 2n=28 with two sex chromosomes. Again, an electron micrograph of tick cell culture IDE8 is shown in FIG. 1.

The tick cell cultures isolated from *I. scapularis* represent undifferentiated cells that did not display specific function, except the formation of muscle. After several passages, most cultures contain one or two types of cells. The cell lines were not contaminated with symbiotic or pathogenic rickettsiae agents or viruses. Examination of the cells by electron microscope did not reveal any contamination with rickettsiae agents or viruses.

EXAMPLE 2

Maintenance and Description of Human HL60 Promyelocytic Leukemia Cell Cultures

The HL60 human promyelocytic leukemia cell line was derived from leukemic cells of a human patient with promyelocytic leukemia. The cell line and its maintenance are described in detail by the American Type Culture Collection, from which the cell line is distributed (ATCC No. CCL 240). These cells have an immature granulocyte phenotype characteristic of promyeloctic bone marrow cells, but retain the ability to differentiate into more mature granulocytic cells or monocytic cells depending upon the conditions and supplements present in the cell culture medium. For example, HL60 cells may be differentiated in vitro into cells with morphologic and functional characteristics of granulocytes by incubation with 1.25% (v/v) dimethylsulfoxide (DMSO) or retinoic acid, whereas the same cells may be differentiated into monocyte/macrophage-like cells by incubation in culture medium containing PMA.

The HL60 cells are preferably cultured in suspension in a tissue culture medium, such as RPMI 1640 supplemented with 5.0 to 20% (v/v) heat-inactivated fetal bovine serum and 2.0 mM L-glutamine. Antibiotics, such as penicillin with streptomycin, or gentamicin may be added for maintenance bacterial cultures to suppress bacterial contamination, as is standard in the art. The doubling time of the cultures under these conditions is approximately 48 to 72 hr, and thus cell concentration must be carefully maintained, preferably below $1.0 \times 10^7$ cells per ml of tissue culture medium. Cell culture medium is preferably partially replaced 2 to 3 times per week with freshly prepared medium.

EXAMPLE 3

Infection of Tick Cell Culture with *Ehrlichia equi*

Cell line IDE8, derived from embryos of the black-legged tick, *Ixodes scapularis*, was infected with neutrophil-derived stages of *E. equi*. In tick cell cultures, the rickettsiae developed into stages and forms unlike those seen in granulocytic white blood cells of the mammalian host. Equine buffy coat cells from whole EDTA-anticoagulated blood of a horse infected with *E. equi* was used as the inoculum. Venous blood was collected from a horse that had been experimentally infected with the MRK isolate of *E. equi* at a time when approximately 8.0% of the peripheral blood leukocytes contained morulae by Wright staining. Blood was collected into tubes containing EDTA or heparin as the anticoagulant. Blood containing acid citrate dextrose (ACD) as the anticoagulant was not suitable for the isolation of *E. equi* into tick cell culture. Established cultures of IDE8 cells in 25 cm² tissue culture flasks were inoculated with buffy coat cells harvested from 8 to 12 ml of horse blood. The medium was L15B medium (Munderloh et al, *Exp. Appl. Acarology*, 7:219 (1989)) supplemented with 5.0% (v/v) heat-inactivated fetal bovine serum, 10% (w/v) tryptose phosphate broth, 0.1% (w/v) lipoprotein concentrate, 0.25% (w/v) NaHCO$_3$, and 10 mM MOPS. Cultures were incubated at 34° C. in a candle jar to provide an atmosphere of reduced O$_2$ (17%) and increased CO$_2$ (3%) tension. This was important, because the Ehrlichiae did not multiply under normal atmospheric conditions. The culture medium (5.0 ml per flask) was replaced once a week, and residual blood inoculum was removed gradually during medium changes. Cell samples were removed by resuspending the entire culture in growth medium. 0.2 ml of cell suspension was mixed with 0.5 ml of a balanced salt solution, and samples thereof were centrifuged onto microscope slides. Slides were fixed twice in methanol, and stained in 8.0% (w/v) Giemsa stain in buffer (pH 6.5 to 6.8).

The *E. equi* isolate has been continuously maintained in IDE8 cultures for 3 passages over 4 months. Infected cells containing large colonies of organisms can sometimes be seen by phase contrast microscopy. There is considerable cytopathic effect on the tick host cells, and in IDE8 cultures, maximally 50 to 60 of the cell population becomes infected. *Ehrlichia equi* is passaged by transferring 0.5 ml of an infected to an uninfected cell layer every 3 to 4 weeks. The first subculture was made 6.5 weeks after initiation in vitro in IDE8 cells.

Identity of *E. equi* was confirmed using a DNA oligonucleotide primers ge9f (SEQ ID NO:1); and ge10r (SEQ ID NO:2), by a standard PCR.

Figure 5:
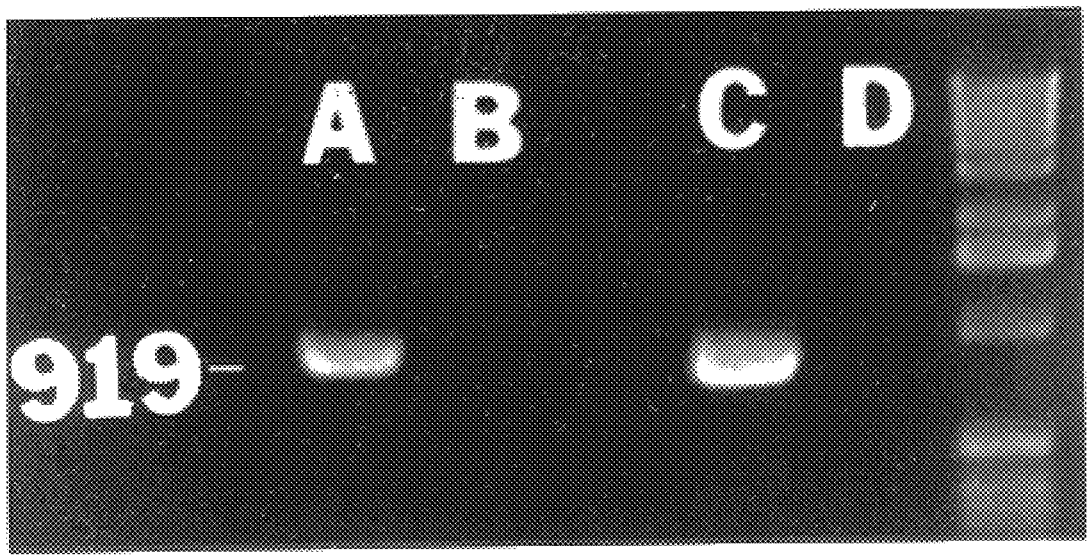
Figure 6A:
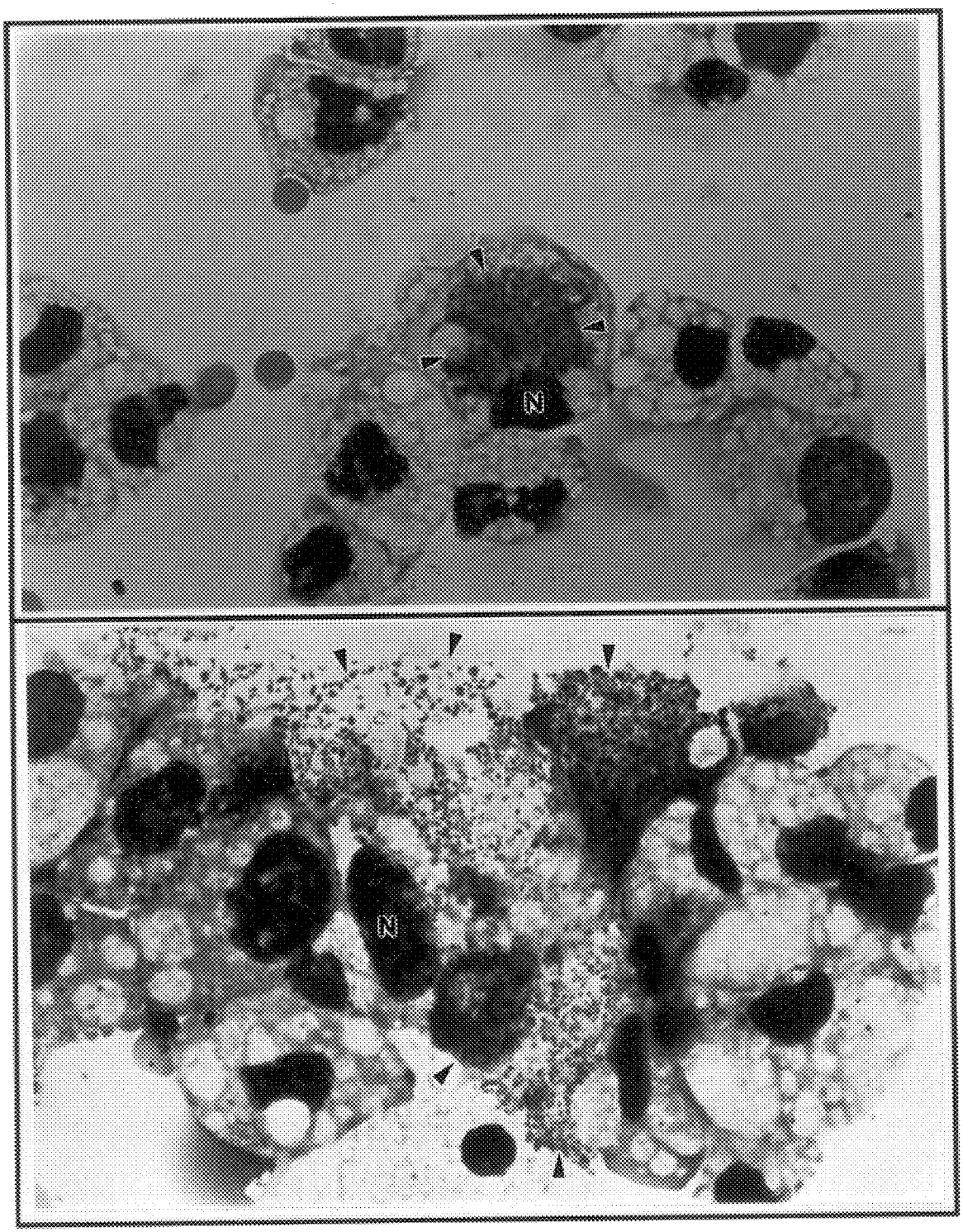
Figure 6B:
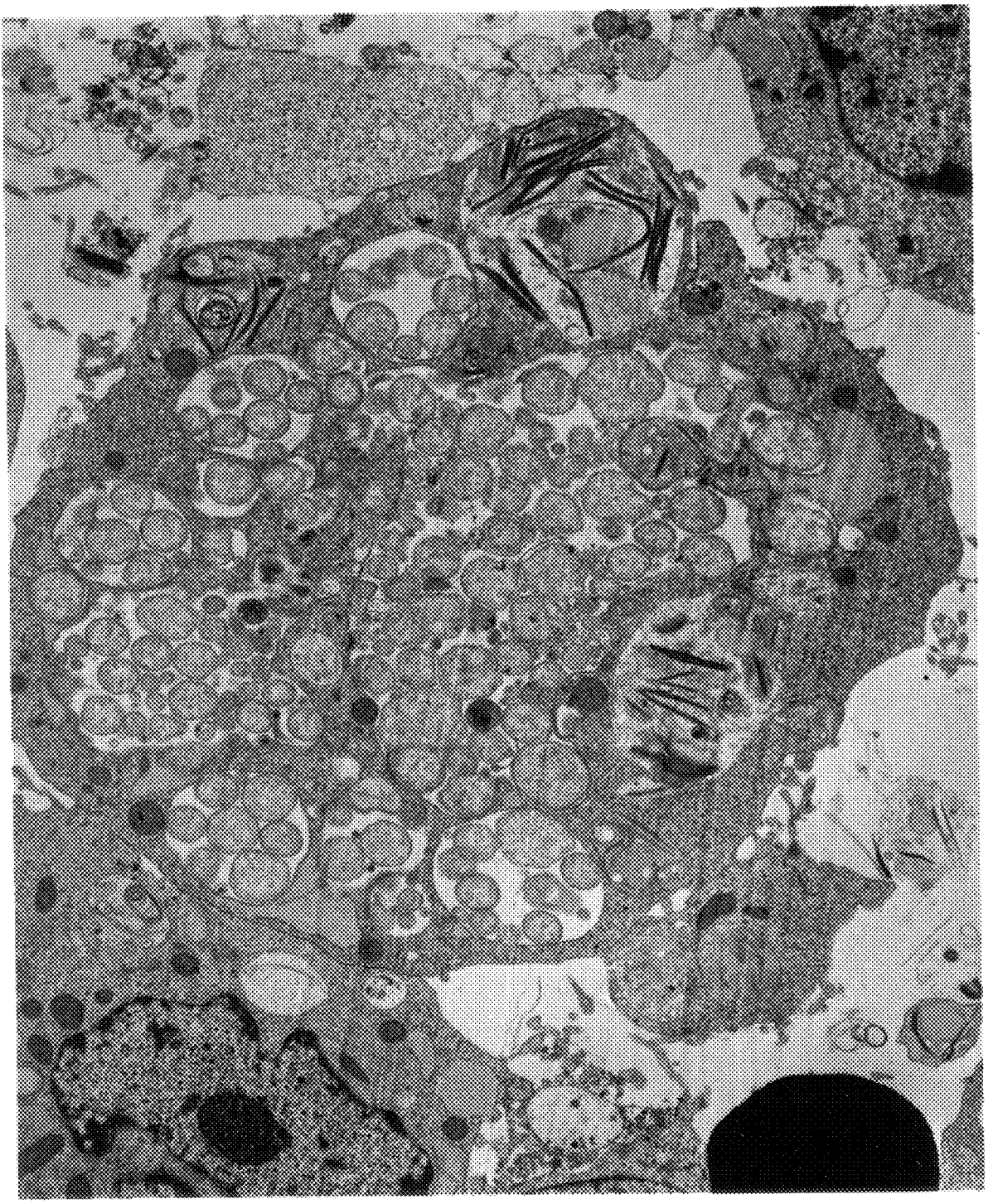
Figure 7A:
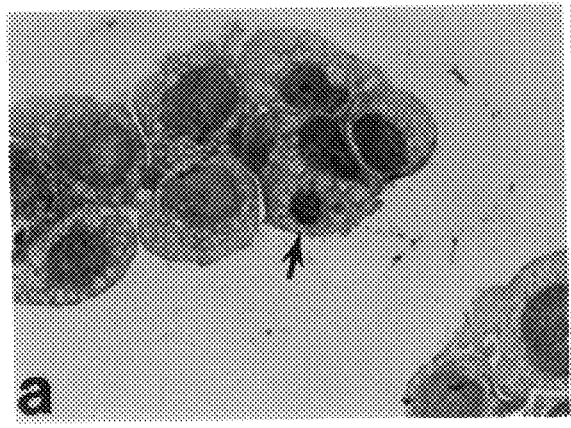
Figure 7B:
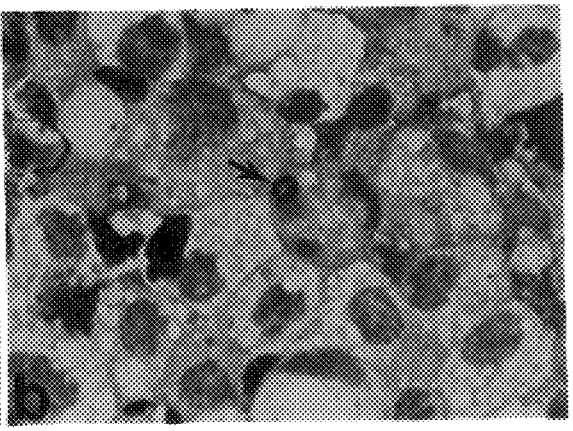
Figure 7C:
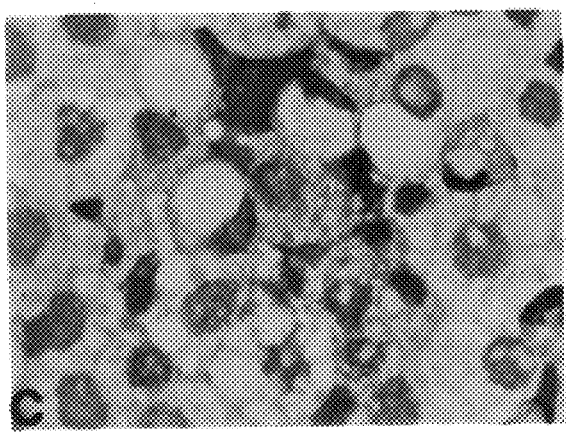
Figure 7D:
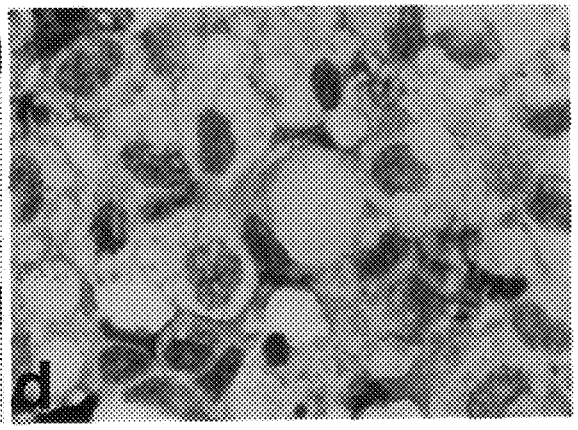
Figure 7E:
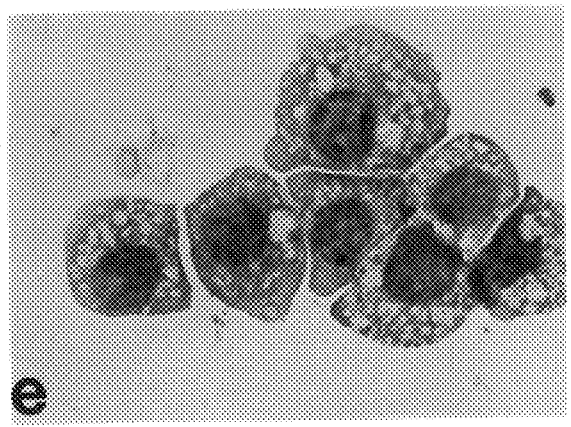
Figure 7F:
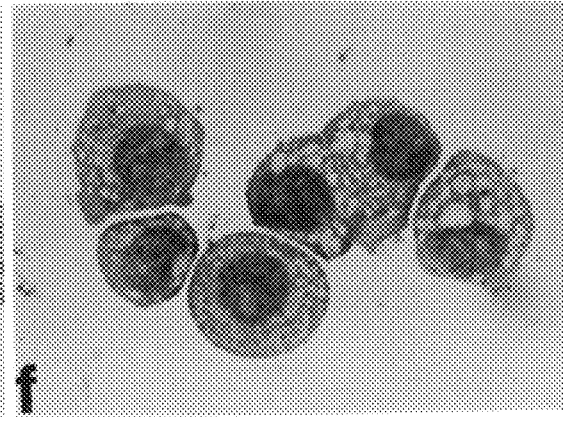
Figure 8A:
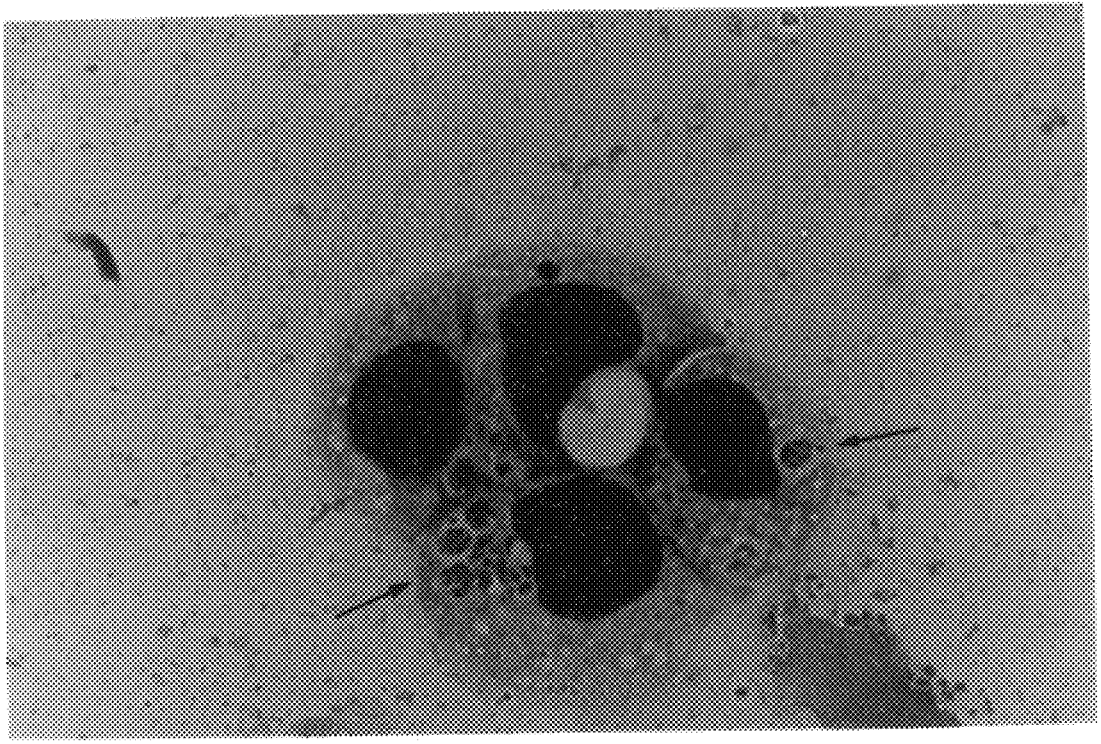
Figure 8B:
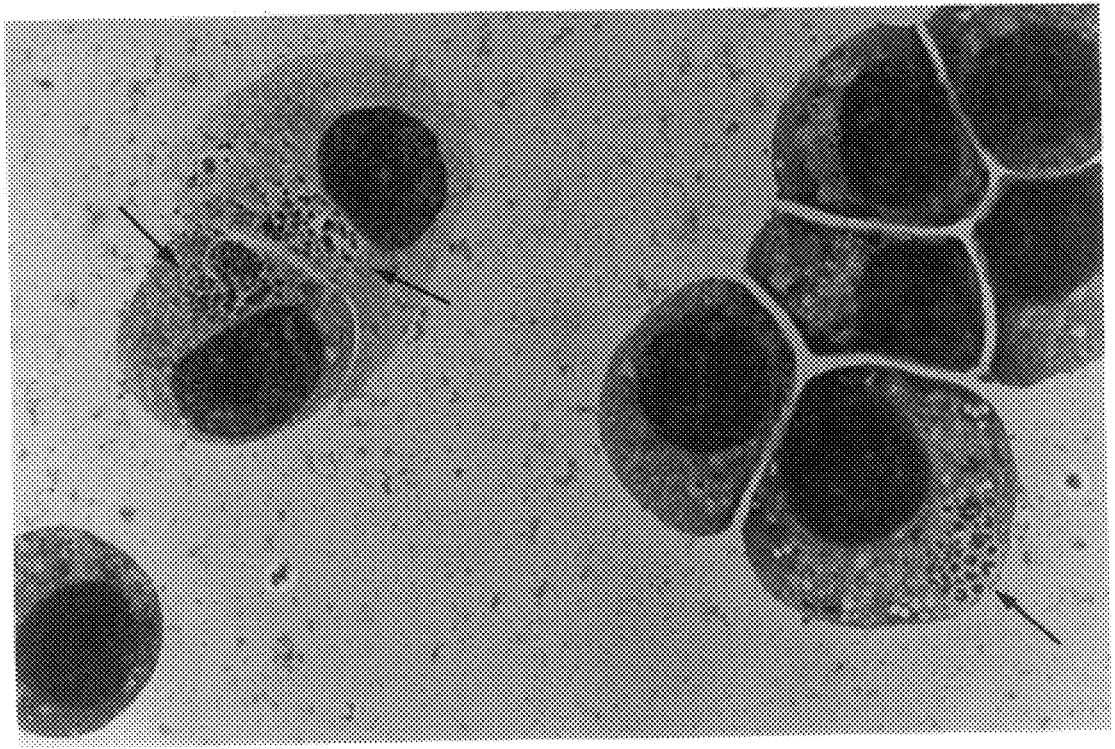

As shown in FIG. 5, Ep group granulocytic Ehrlichiae-specific oligonucleotide primers amplified a single product of the expected size, 919 base pairs.

The antigenic identity of the *E. equi* in IDE8 tick cultures was also confirmed by an immunocytology using polyclonal horse anti-*E. equi* and polyclonal human anti-human granulocytic ehrlichiosis agent antibodies (see Example 5 below).

PCR using infected tick cell culture extract as a template confirmed the identity of the *E. equi* growing in IDE8 cells. A crude lysate was made according to rapid sample preparation for PCR (Higuchi, In: *PCR Technology, Principles and Applications for DNA Amplification*, H. A. Ehrlich, Ed. Stockton Press, New York, Chapter 4 (1989)). Briefly, infected tick cells from one culture were forced about 10 times through a 27 gauge needle, and large debris removed by centrifugation at 100×g. The supernatant fluid containing small particles and Ehrlichiae was collected by centrifugation at 10,000×g for 20 min, and the pellet resuspended in lysis buffer with NP-40, Tween-20 and Proteinase K (Higuchi, supra). Following incubation at 55° C. for 1 hr, the proteinase was inactivated (95° C. for 20 min), and the lysate stored at −20° C. Uninfected IDE8 cells were extracted the same way as a control. 10 µl of this lysate were used as a template in the PCR with primers ge9f and ge10r at a concentration of 0.5 µM each. 100 µl reaction mixtures containing 1.5 mM MgCl$_2$ and 0.2 mM of the four deoxynucleotides were cycled 30 times through 92° C. for 1 min, 56° C. for 0.5 min and 72° C. for 1 min. 10 µl of the resulting DNA was mixed with loading buffer (Ficoll 400 with bromophenol blue), and electrophoresed through 0.9% (w/v) agarose in 0.5X TBE (Tris-Borate-EDTA) buffer at 150 volts until adequately separated. The gel was stained with ethidium bromide and photographed under UV light (see FIG. 5). Lysate from infected IDE8 cultures gave rise to a DNA product of the expected size, 919 bp, while control lysate did not, indicating the presence of *E. equi* DNA and thus, *E. equi* in the infected cultures. A plasmid encoding the entire *E. equi* 16S ribosomal RNA gene was used as positive control and produced an identical 919 bp band, while a negative control using no template produced no detectable band.

EXAMPLE 4

Infectivity for Horses of *Ehrlichia equi* Propagated in IDE8 Tick Cell Cultures

*Ehrlichia equi* cultured in IDE8 tick cell cultures is infectious and pathogenic for horses. 5.0 ml of a culture in which 48.6% of the cells were infected, as judged by Giemsa-stained cell spreads, were inoculated intravenously into an 11-year old thoroughbred gelding. This horse was seronegative for prior infection with *E. equi*, as judged by the absence of antibody by the IFA test using *E. equi*-infected horse leukocytes as the antigen. A PCR test that detects the presence of Ep group granulocytic Ehrlichiae 16S ribosomal RNA gene nucleotide sequences in the blood also was negative.

On day 6 post-inoculation, the body temperature of the horse began to rise, and on day 8, PCR for Ep group DNA using Ep specific primers EE3 (SEQ ID NO:3) and EE4 (SEQ ID NO:4) showed the presence of the typical 928 base pair DNA fragment indicative of active *E. equi* infection, and 1.0% of the peripheral blood neutrophils contained morphologically typical morulae. The horse then became acutely febrile, with temperatures rising maximally to 104.8° F. The horse was anorectic, developed petechiae and icterus of the mucous membranes, limb edema and diarrhea, all typical signs of acute equine granulocytic ehrlichiosis caused by E. equi. When 20% of the peripheral blood leukocytes contained morulae, 20 ml of blood was drawn into tubes containing EDTA as anticoagulant. Ehrlichia equi was again isolated in IDE8 cell culture from this second blood sample. The horse was treated with tetracycline antibiotics to save its life. A second E. equi-seronegative horse was inoculated intravenously with 5.0 ml of an uninfected culture of IDE8 cells. After 14 days, this control horse remained healthy and afebrile.

EXAMPLE 5

Antibody Reactivity with Ehrlichia equi Grown in IDE8 Cell Culture

Figure 10A:
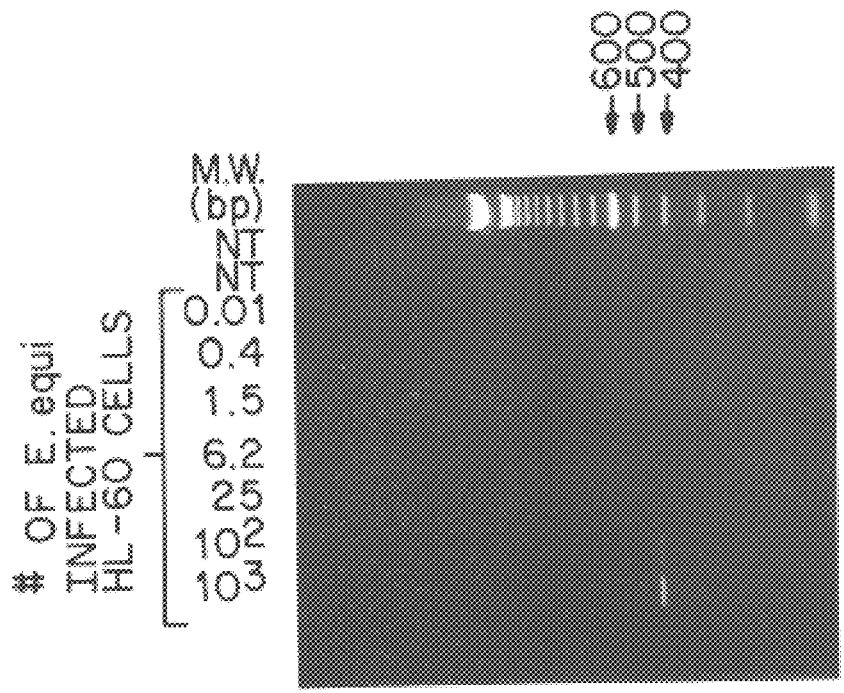
Figure 10B:
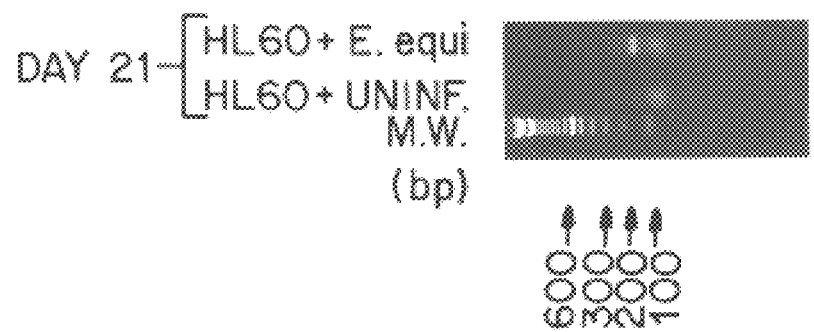

Immunocytologic identification was accomplished by preparing centrifuged slide samples of E. equi-infected IDE8 tick cells (prior to first passage), and fixing for 10 min in methanol, twice. Slides were air-dried, and incubated with blocking buffer comprising phosphate buffered saline with 0.5% (v/v) non-fat dry milk and 5.0% (v/v) normal goat serum for 10 min. The residual buffer was drained, and replaced on individual slide preparations by horse anti-E. equi or human anti-HGE agent diluted 1:80 in blocking buffer. These antibodies were previously shown to have high titers of E. equi antibodies by indirect fluorescent antibody and immunoblot assays. In addition, control nonimmune horse and human sera were similarly diluted and incubated on identically treated slides. Uninfected IDE8 cells were tested with each of these antibody and control antibody preparations for specificity. The diluted primary antibody solutions were incubated on the slides for 1 hr at room temperature, and the slides were thoroughly washed in PBS. The secondary antibodies used were biotinylated goat anti-horse IgG, IgA, and IgM and biotinylated goat anti-human IgG, IgA, and IgM. Each was incubated on the appropriate slide for 1 hr at room temperature before washing the slides in PBS as described above. Each slide was then incubated with streptavidin-alkaline phosphatase, diluted in blocking buffer, for 30 min, washed, and bound antibody complex was detected by incubation in naphthol phosphate buffer with AS/MX Fast red substrate for 10 min. The reaction was terminated by a water wash, and the slides were counter-stained with Meyer's hematoxylin, covered with Crystal Mount (Biomeda, Foster City, Calif.), dried, and mounted with coverslips. Reaction product on *E. equi* in infected cells was detected by light microscopy.

The results of immunocytologic staining are shown in FIGS. 7A–7F. FIG. 7A demonstrates the presence of intra-cytoplasmic staining of aggregates (morulae) of *E. equi* in IDE8 tick cells recognized by binding with a polyclonal serum antibody obtained from a patient who was convalescent from PCR proven and serologically proven HGE. FIG. 7B shows a similar profile of intracytoplasmic staining of *E. equi* morulae horse *E. equi* antibody by a polyclonal serum antibody. FIGS. 7C and 7D represent the same IDE8 *E. equi*-infected cells reacted with nonimmune serum from a human and horse subject, respectively, and demonstrate the lack of reactivity of the *E. equi* within the IDE8 cells with serum lacking Ep group granulocytic Ehrlichiae antibodies. FIGS. 7E and 7F represent uninfected IDE8 cells reacted with the polyclonal human anti-HGE agent sera, and the polyclonal horse anti-*E. equi*, respectively. The lack of reactivity of these reagents with uninfected IDE8 cells excludes the possibility that these sera contain antibodies reactive with IDE8 tick cell antigens that might mimic the morphology of *E. equi* morulae.

EXAMPLE 6

Infection of Human HL60 Promyelocytic Leukemia Cells with *Ehrlichia equi* Derived from Infected IDE8 Cells The HL60 human promyelocyte cell line (ATCC CCL 240) was propagated in RPMI 1640 medium with 10% (v/v) fetal bovine serum, 2.0 mM L-glutamine, penicillin and streptomycin. Log phase HL60 cells were centrifuged, counted, and resuspended into fresh medium without penicillin and streptomycin at a cell density of $3\times10^6$ cells per ml. *Ixodes scapularis* IDE8 tick cells, of which 30% contained *E. equi* morulae, were resuspended in tick cell culture medium and 0.25 ml were inoculated into 25 $cm^2$ plastic tissue culture flasks containing 9.0 ml of HL60 cells. Similarly, an equivalent inoculum of uninfected IDE8 cells was incubated with 9.0 ml of HL60 cells, and a 9.0 ml volume of HL60 cells was held as an uninoculated control. The flasks were maintained in an atmosphere of 5% $CO_2$ at 37° C. Cell cultures were examined weekly by removing small aliquots and preparing cytocentrifuged slides that were then examined microscopically after Giemsa staining. Aliquots of the same cells were stored for later examination to detect the presence of Ehrlichiae species and Ep group granulocytic Ehrlichiae DNA.

At days 0 and 7, control HL60 cells, control HL60 cells inoculated with uninfected IDE8 cells, and HL60 cells inoculated with *E. equi*-infected IDE8 tick cells appeared identical, except for the presence of occasional large, more rectangular tick cells among the HL60 leukemia cells. At day 14, no significant differences were noted between the 3 groups. By 21 days after inoculation, typical intracytoplasmic inclusions (morulae) filled with individual bacterial bodies (Ehrlichiae) were present within vacuoles of 3.0% of cells in the flask of HL60 cells inoculated with *E. equi*-infected IDE8 tick cells. No morulae were noted in either of the control HL60 flasks. At days 28 to 42, morulae were present in from 10 to 16% of cells, and cell clumping was frequently observed in the suspension cultures. By day 49, 27% of cells contained definite morulae, and in many cases multiple, with complex internal structure in various stages from discrete organisms to large aggregates, and in some instances appearing to cause cell lysis and subsequent extra-cellular release of organisms (see FIGS. 8A–8B). Control cells contained no such structures. The morphology of many of these morulae, especially in the earlier cultures, is quite similar to those seen in the peripheral blood neutrophils in human granulocytic ehrlichiosis in that these appeared to have generally even, rounded contours within the apparent cytoplasmic vacuoles.

The identity of the infecting bacterium was confirmed as Ehrlichiae species, and then as an Ep group granulocytic Ehrlichiae by the PCR. The cultures were first studied using primers designed based upon the 16S ribosomal RNA gene sequence PER1 (SEQ ID NO:7) and PER2 (SEQ ID NO:8). These primers amplify a 450 base pair product from both *E. equi* and *E. canis* (FIG. 10A, lanes 1–4), and were used to assay for the presence of Ehrlichiae species DNA in the HL60 cell cultures inoculated with *E. equi*-infected IDE8 cells 56 days after inoculation. Cells from this flask were centrifuged and washed 3 times in fresh tissue culture medium, counted, and the DNA was extracted using chaotropic lysis with guanidium isothiocyanate. PCR was performed on serial dilutions of the DNA isolated from these cells. Ehrlichiae species DNA was amplified and detected in ethidium bromide stained agarose gels when DNA from only 6.25 cells was used as the initial DNA PCR template. The signal strength of this PCR-amplified DNA band was equivalent to approximately 100 molecules of the 16S ribosomal RNA gene as determined in other experiments (FIG. 10A). Using an DNA probe constructed to anneal within the fragment of Ehrlichiae species DNA in a Southern blot, signal could be detected when DNA from as few as 0.4 but not 0.01 cells was assayed. The specific identity of the Ehrlichiae agent as *E. equi*, a member of the Ep group granulocytic Ehrlichiae was confirmed by PCR amplification with a set of Ep group-specific primers, GER3 (SEQ ID NO:5) and GER4 (SEQ ID NO:6) (FIG. 10B). This set of primers amplified a 150 base pair fragment of the Ep group 16S ribosomal RNA gene in DNA obtained from HL60 cells inoculated with *E. equi*-infected IDE8 tick cells first at day 21 after inoculation. Ep group DNA was not detected in control cultures at any time.

Figure 9A:
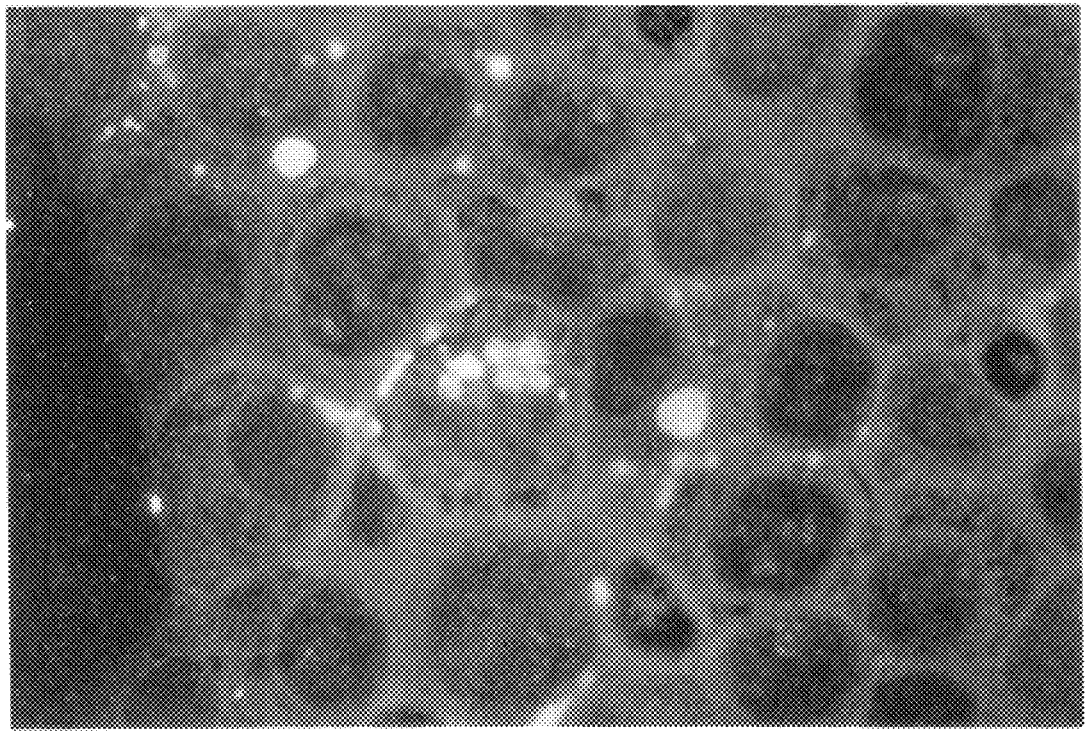
Figure 9B:
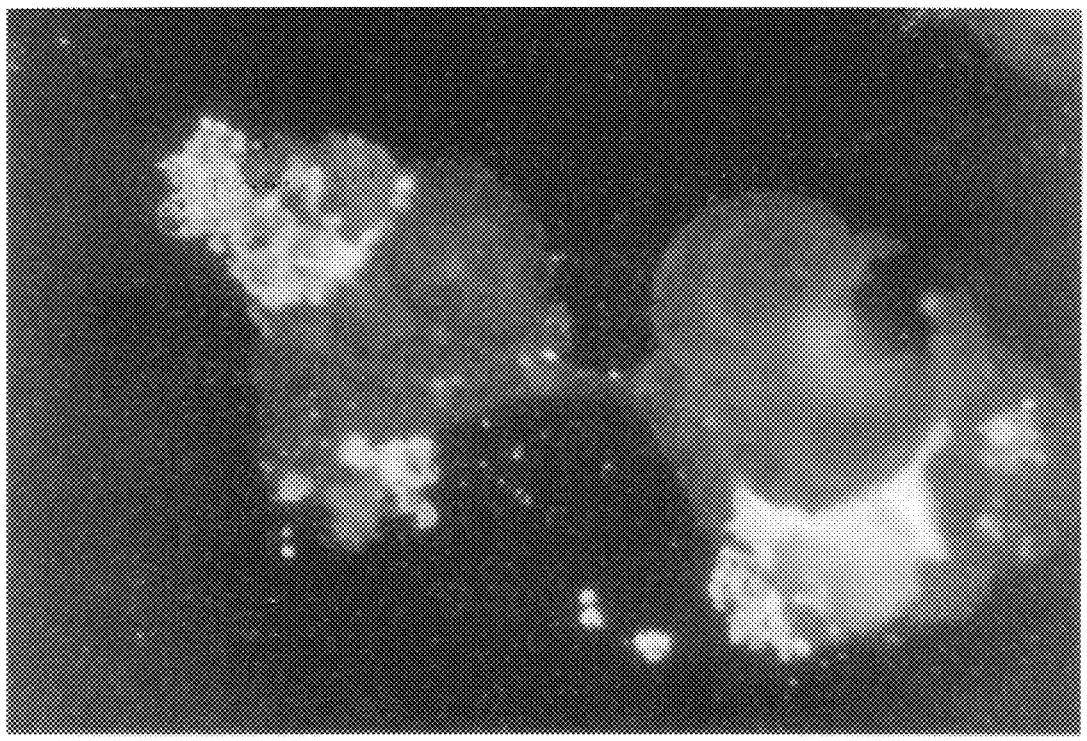

The infection of the HL60 cells was further confirmed by an indirect fluorescent antibody method using serum obtained from a patient convalescent from HGE. After a blocking antibody step with normal rabbit serum, the patient serum and a control serum were used as the primary antibody at a 1:20 dilution and reacted with *E. equi*-infected HL60 cells followed by reaction with fluorescein conjugated Fab fragments of anti-human immunoglobulins. The patient serum, but not the control, fluoresced brightly in a pattern corresponding to the cytoplasmic structures clearly identifiable as morulae (FIGS. 9A–9B).

While the invention has been described in detail, and with reference to specific embodiments thereof, it will be apparent to one of ordinary skill in the art that various changes and modifications can be made therein without departing from the spirit and scope thereof.

We claim:

1. A method of diagnosing human granulocytic ehrlichiosis (HGE) in a human patient comprising the steps of:
   (a) providing an infected HL60 cell culture, wherein the HL60 cell culture is infected with an *Ehrlichia phagocytophila* genogroup organism,
   (b) incubating the infected cells with antiserum from said patient, and
   (c) diagnosing HGE in said patient by detecting immunoreaction of the antiserum from said patient with the infected HL60 cell culture.

2. The method of claim 1, wherein said *Ehrlichia phagocytophila* genogroup organism is *Ehrlichia equi*.

3. The method of claim 1, wherein said immunoreaction is detected by an indirect immunofluorescence method, an indirect immunoenzymatic method, latex agglutination, or complement fixation.

4. The method of claim 1, wherein 100 to 1000 HL60 cells are present on a slide, and wherein no less than 20% of the HL60 cells are infected with *Ehrlichia phagocytophilia*.

5. The method of claim 4, wherein about 50–100% of the HL60 cells are infected with *Ehrlichia phagocytophilia*.

* * * * *